(12) United States Patent
Lan et al.

(10) Patent No.: US 9,487,506 B2
(45) Date of Patent: Nov. 8, 2016

(54) MINERALOCORTICOID RECEPTOR ANTAGONISTS

(75) Inventors: Ping Lan, Plainsboro, NJ (US); Kun Liu, Edison, NJ (US); Anthony Ogawa, New Providence, NJ (US); Hong Shen, West Windsor, NJ (US); Christine Yang, Jersey City, NJ (US); Yuguang Wang, Shanghai (CN); Richard Beresis, Shanghai (CN); Changhe Qi, Shanghai (CN)

(73) Assignee: Merck Sharp & Dohme Corp., Rahway, NJ (US)

(*) Notice: Subject to any disclaimer, the term of this patent is extended or adjusted under 35 U.S.C. 154(b) by 13 days.

(21) Appl. No.: 14/110,441

(22) PCT Filed: Apr. 11, 2012

(86) PCT No.: PCT/CN2012/073795
§ 371 (c)(1),
(2), (4) Date: Oct. 8, 2013

(87) PCT Pub. No.: WO2012/139495
PCT Pub. Date: Oct. 18, 2012

(65) Prior Publication Data
US 2014/0336224 A1 Nov. 13, 2014

Related U.S. Application Data

(60) Provisional application No. 61/474,816, filed on Apr. 13, 2011.

(51) Int. Cl.
| C07D 413/06 | (2006.01) |
| A61K 31/4245 | (2006.01) |
| C07D 401/04 | (2006.01) |
| A61K 31/4439 | (2006.01) |
| C07D 231/56 | (2006.01) |
| A61K 31/416 | (2006.01) |

(52) U.S. Cl.
CPC .......... *C07D 413/06* (2013.01); *A61K 31/416* (2013.01); *A61K 31/4245* (2013.01); *A61K 31/4439* (2013.01); *C07D 231/56* (2013.01); *C07D 401/04* (2013.01)

(58) Field of Classification Search
None
See application file for complete search history.

(56) References Cited

U.S. PATENT DOCUMENTS

| 4,342,767 A | 8/1982 | Albers-Schonberg et al. |
| 4,346,227 A | 8/1982 | Terahara et al. |
| 4,444,784 A | 4/1984 | Hoffman et al. |
| 4,845,079 A | 7/1989 | Luly et al. |
| 4,885,292 A | 12/1989 | Ryono et al. |
| 4,894,437 A | 1/1990 | TenBrink |
| 4,980,283 A | 12/1990 | Huang et al. |
| 5,034,512 A | 7/1991 | Hudspeth et al. |
| 5,036,053 A | 7/1991 | Himmelsbach et al. |
| 5,036,054 A | 7/1991 | Kaltenbronn et al. |
| 5,055,466 A | 10/1991 | Weller, III et al. |
| 5,063,207 A | 11/1991 | Doherty et al. |
| 5,063,208 A | 11/1991 | Rosenberg et al. |
| 5,064,965 A | 11/1991 | Ocain et al. |
| 5,066,643 A | 11/1991 | Abeles et al. |
| 5,071,837 A | 12/1991 | Doherty et al. |
| 5,075,451 A | 12/1991 | Ocain et al. |
| 5,089,471 A | 2/1992 | Hanson et al. |
| 5,095,119 A | 3/1992 | Ocain et al. |
| 5,098,924 A | 3/1992 | Poss |

(Continued)

FOREIGN PATENT DOCUMENTS

| DE | 102007028521 | 12/2008 |
| WO | 9723200 | 7/1997 |

(Continued)

OTHER PUBLICATIONS

Danziger, Automated Site-Directed Drug Design: A General Algorithm for Knowledge Acquisition about Hydrogen-Bonding Regions at Protein Surfaces, Proceedings of the Royal Society of London. Series B, Biological Sciences, 1989, 236(1283), pp. 101-113.*

(Continued)

*Primary Examiner* — San-Ming Hui
*Assistant Examiner* — Andrew Lee
(74) *Attorney, Agent, or Firm* — Patricia A. Shatynski; Catherine D. Fitch

(57) ABSTRACT

Compounds of the Formula (I) as well as pharmaceutically acceptable salts thereof, that may be useful for treating aldosterone-mediated diseases are disclosed. Processes for preparing compounds of the Formula (I), use of the compounds for the therapy and prophylaxis of the abovementioned diseases and for preparing pharmaceuticals for this purpose, and pharmaceutical compositions which comprise compounds of the Formula (I) are disclosed.

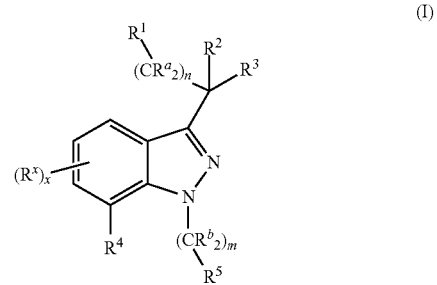

4 Claims, No Drawings

(56) References Cited

U.S. PATENT DOCUMENTS

| | | | |
|---|---|---|---|
| 5,104,869 | A | 4/1992 | Albright et al. |
| 5,106,835 | A | 4/1992 | Albright et al. |
| 5,114,937 | A | 5/1992 | Hamby et al. |
| 5,116,835 | A | 5/1992 | Ruger et al. |
| 5,260,440 | A | 11/1993 | Hirai et al. |
| 5,273,995 | A | 12/1993 | Roth |
| 5,354,772 | A | 10/1994 | Kathawala |
| 7,410,992 | B2 | 8/2008 | Chen et al. |
| 2006/0030612 | A1 | 2/2006 | Steffan et al. |
| 2009/0197882 | A1* | 8/2009 | Buchstaller et al. ...... 514/234.5 |
| 2010/0234601 | A1 | 9/2010 | Halland et al. |
| 2010/0256137 | A1 | 10/2010 | Buchstaller et al. |

FOREIGN PATENT DOCUMENTS

| | | |
|---|---|---|
| WO | 9728149 | 8/1997 |
| WO | 0208188 | 1/2002 |
| WO | 0217895 | 3/2002 |
| WO | 2004020408 | 3/2004 |
| WO | 2004020409 | 3/2004 |
| WO | WO2004067529 | 8/2004 |
| WO | WO2005012326 | 2/2005 |
| WO | WO2006057946 | 6/2006 |
| WO | WO 2008019968 A1 * | 2/2008 |
| WO | WO2008118319 | 10/2008 |

OTHER PUBLICATIONS

Castren et al., J. of Neuroendocrinology vol. 3, (1993) pp. 461-466.
Pitt et al., N. Engl. J. Med. vol. 341(10), (1999) pp. 709-717.
Pitt et al., N. Engl. J. Med. vol. 348(14) (2003) pp. 1309-1321.
Funder, J. W., Hypertens. Res. vol. 33(6) (2010) pp. 539-540.
Calhoun et al., J. Am. Soc. Hypertens, vol. 2(6) (2008) pp. 462-468.
Huang et al., Am. J. Physiol. Heart Circ. vol. 2 (2010) pp. H422-H430.
The Rales Investigators, Am. J. Cardiol. vol. 78 (1996) pp. 902-907.
Pitt et al., Circulation vol. 118(16) (2008) pp. 1643-1650.
Bomback et al., Clin. Nephrol. vol. 72(6), (2009) pp. 449-456.
Williams, J. S., Nat. Rev. Endocrinol. vol. 6(5), (2010) pp. 248-250.
Nishizaka et al., Curr. Hypertens. Rep. vol. 7(5), (2005) pp. 343-347.
Gaddam et al., Hypertension, vol. 55(5), (2010), pp. 1137-1142.
Zannand et al., Eur. J. Heart Fail. vol. 12(6), (2010) pp. 617-622.
Takai et al., Hypertension vol. 46(5), (2005) pp. 1135-1139.
Tirosh et al., Curr. Hypertens Rep. vol. 12(4), (2010) pp. 252-257.
Hadley, M. E., Endocrinology, 2nd Ed. pp. 366-381 (1988).
Brilla et al., Journal of Molecular & Cellular Cardiology, vol. 25(5), (1993) pp. 563-575.
International Search Report—Mailing date: Jul. 19, 2012.
Clark, B.J., et al: "Synthesis of 4 Arylmethyl-1 2 3 Benzotriazines", Journal of Chemical Research, Science Reviews Ltd., GB, No. 10, Jan. 1, 1981, pp. 324.
Guiyong Wu, et al., "One-pot synthesis of useful heterocycles in medicinal chemistry using a cascade strategy", Green Chemistry, vol. 14, No. 3, Jan. 1, 2012, p. 580.
Pamela G. Alsabeh, et al. "Palladium-catalyzed synthesis of indoles via ammonia cross-coupling-alkyne cyclization", Chemical Communications, vol. 47, No. 24, Jan. 1, 2011, p. 6936.
Vasilevsky, et al.:"Cyclocondensationof activated ortho-chloroarylacetylenes with hydrazine: a novel route to substituted indazoles", Mendeleev Communicacations, Institute of Physics Publishing, Bristol, GB, vol. 6, No. 3, Jan. 1, 1996, pp. 98-99.

* cited by examiner

MINERALOCORTICOID RECEPTOR ANTAGONISTS

CROSS REFERENCE TO RELATED APPLICATIONS

This application is the National Stage of International Application No. PCT/CN2012/073795 filed on Oct. 18, 2012, which claims the benefit under 35 U.S.C. 119(e) of U.S. Provisional Application No. 61/474,816, filed Apr. 13, 2011.

BACKGROUND OF THE INVENTION

The Mineralocorticoid Receptor (MR) is a nuclear hormone receptor that is activated by aldosterone and regulates the expression of many genes involved in electrolyte homeostasis and cardiovascular disease. Increased circulating aldosterone increases blood pressure through its effects on natriuresis, with potentially additional effects on the brain, heart and vasculature. In addition, hyperaldosteronism have been linked to many pathophysiological processes resulting in renal and cardiovascular disease. While hyperaldosteronism is commonly caused by aldosterone-producing adenomas, resistant hypertensive patients frequently suffer from increased aldosterone levels often termed as "Aldosterone Breakthrough" as a result of increases in serum potassium or residual AT1R activity. Hyperaldosteronism and aldosterone breakthrough typically results in increased MR activity and MR antagonists have been shown to be effective as anti-hypertensive agents and also in the treatment of heart failure and primary hyperaldosteronism.

In addition, in visceral tissues, such as the kidney and the gut, MR regulates sodium retention, potassium excretion and water balance in response to aldosterone. MR expression in the brain also appears to play a role in the control of neuronal excitability, in the negative feedback regulation of the hypothalamic-pituitary-adrenal axis, and in the cognitive aspects of behavioral performance (Castren et al., J. of Neuroendocrinology, 3, 461-66 (1993)).

Eplerenone and spironolactone are two MR antagonists that have been shown to be efficacious in treating cardiovascular disease, particularly hypertension and heart failure (RALES Investigators (1999) The Effect of Spironolactone on Morbidity and Mortality in Patients with Severe Heart Failure, N. Engl. J. Med., 1999, 341(10):709-717; Pitt B, et al., EPHESUS investigator (2003) Eplerenone, a Selective Aldosterone Blocker, in Patients with Left Ventricular Dysfunction After Myocardial Infarction, N. Engl. J. Med., 348(14):1309-1321; Funder J W., (2010) Eplerenone in Chronic Renal Disease: the EVALUATE trial, Hypertens. Res., 33(6):539-40). Moreover, multiple studies have shown that treatment with spironolactone or eplerenone significantly lower systolic blood pressure in mild-moderate, obese, systolic, PHA, and resistant hypertensive patients (Calhoun D A, et al., (2008) Effectiveness of the Selective Aldosterone Blocker, Eplerenone, in Patients with Resistant Hypertension, J. Am. Soc. Hypertens., 2008 November-December; 2(6):462-8; Huang B S, et al., (2010) Central Neuronal Activation and Pressor Responses Induced by Circulating ANG II: role of the brain aldosterone-"ouabain" pathway, Am. J. Physiol. Heart. Circ. Physiol., (2):H422-30; The RALES Investigators. (1996) Effectiveness of Spironolactone added to an Angiotensin-converting enzyme Inhibitor and a Loop Diuretic for Severe Chronic Congestive Heart Failure, (The Randomized Aldactone Evaluation Study [RALES]), Am. J. Cardiol., 1996; 78:902-907; Pitt B, et al., EPHESUS Investigators, Serum potassium and clinical outcomes in the Eplerenone Post-Acute Myocardial Infarction Heart Failure Efficacy and Survival Study (EPHESUS), Circulation, 2008 Oct. 14; 118(16):1643-50; Bomback A S et al., (2009), Low-dose spironolactone, added to long-term ACE inhibitor therapy, reduces blood pressure and urinary albumin excretion in obese patients with hypertensive target organ damage, Clin. Nephrol., 72(6):449-56; Williams J S, Hypertension: spironolactone and resistant hypertension, Nat. Rev. Endocrinol., 2010 May; 6(5):248-50; Nishizaka M K, et al., The role of aldosterone antagonists in the management of resistant hypertension. Curr Hypertens Rep. 2005 October; 7(5):343-7. Review; Gaddam K, et al., (2010) Rapid reversal of left ventricular hypertrophy and intracardiac volume overload in patients with resistant hypertension and hyperaldosteronism: a prospective clinical study, Hypertension, 55(5):1137-42; Zannad F, et al., (2010) Rationale and design of the Eplerenone in Mild Patients Hospitalization And Survival Study in Heart Failure (EMPHASIS-HF), Eur. J. Heart Fail., 12(6):617-22).

Evidence in preclinical models also suggest that MR antagonists would be efficacious in treating the metabolic syndrome and atherosclerosis (Takai, S. et al, (2005) Eplerenone inhibits atherosclerosis in nonhuman primates. Hypertension. 46(5):1135-9; Tirosh, A. et al., GK. (2010) Mineralocorticoid receptor antagonists and the metabolic syndrome. Curr Hypertens Rep. 2010 August; 12(4):252-7).

Also, published PCT application WO 2002/17895 disclosed that aldosterone antagonists may be useful in the treatment of subjects suffering from one or more cognitive dysfunctions including, but not limited to psychoses, cognitive disorders (such as memory disturbances), mood disorders (such as depression and bipolar disorder), anxiety disorders and personality disorders.

Elevation in aldosterone levels, or excess stimulation of mineralocorticoid receptors, is linked to several physiological disorders or pathologic disease states, including Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, and disorders associated with excess catecholamine levels. (Hadley, M. E., ENDOCRINOLOGY, $2^{nd}$ Ed., pp. 366-81, (1988); and Brilla et al., Journal of Molecular and Cellular Cardiology, 25 (5), pp. 563-75 (1993). Compounds and/or pharmaceutical compositions which act as MR antagonists may be of value in the treatment of any of the above conditions.

Despite significant therapeutic advances in the treatment of hypertension and heart failure, the current standard of care is suboptimal and there is a clear unmet medical need for additional therapeutic/pharmacological interventions. This invention addresses those needs by providing compounds and compositions which may be useful for the treatment or prevention of hypertension, heart failure, other cardiovascular disorders and other aldosterone disorders.

SUMMARY OF THE INVENTION

The present invention relates to compounds which have Mineralocorticoid Receptor (MR) antagonist activity, which may be valuable pharmaceutically active compounds for the therapy and prophylaxis of diseases, for example for treating aldosterone-mediated disorders, including cardiovascular disease. The present invention is directed to compounds of the Formula I:

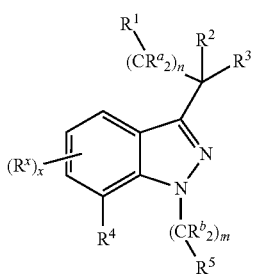

or a pharmaceutically acceptable salt thereof. The invention furthermore relates to methods of treating and preventing the above mentioned diseases and to processes for preparing compounds of the Formula I and for pharmaceutical preparations which comprise compounds of Formula I.

DETAILED DESCRIPTION OF THE INVENTION

The invention concerns compounds of Formula I:

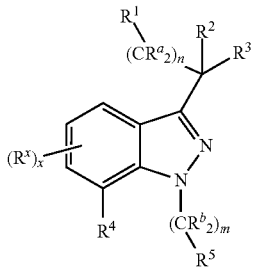

or a pharmaceutically acceptable salt thereof, wherein
Each $R^x$ is independently H, halo, OR, $C_1$-$C_6$ alkyl, $(CR_2)_{0-1}CN$, OR, $C(O)OR^{10}$, $C_3$-$C_{10}$ cycloalkyl, $NR^6C(O)R^{10}$, $NR^6SO_2R^8$, or $NH_2$, said alkyl and cycloalkyl are optionally substituted with 1 to 3 substituents selected from halo, OR and $C_1$-$C_6$ alkyl;
Each R is independently H, $C_1$-$C_6$ alkyl or $C_3$-$C_{10}$ cycloalkyl, said alkyl and cycloalkyl are optionally substituted with 1 to 4 halo substituents;
Each $R^a$ is independently H, $C_1$-$C_6$ alkyl, aryl or $CF_3$, said alkyl and aryl are optionally substituted with 1 to 3 aryl, $CF_3$ or halo substituents;
Each $R^b$ is independently H or $C_1$-$C_6$ alkyl, said alkyl is optionally substituted with 1 to 3 aryl, $CF_3$ or halo substituents;
$R^1$ is
1) H,
2) CN,
3) OR,
4) $C_1$-$C_6$ alkyl,
5) $C_3$-$C_6$ cycloalkyl
6) aryl,
7) heteroaryl,
8) heterocyclyl,
9) $C(O)R^{10}$,
10) $C(O)NRR^6$, or
11) $C(O)OR^{10}$;
wherein said alkyl, cycloalkyl, aryl, heteroaryl and heterocyclyl are optionally substituted with one to three $CF_3$, OR, CN, $C_1$-$C_6$ alkyl, or halo substituents;

$R^2$ is
1) H, Or
2) $C_1$-$C_6$ alkyl, said alkyl is optionally substituted with one to three OR, CN or halo substituents;
$R^3$ is $(CR_2)_t$-aryl or $(CR_2)_t$-heteroaryl, wherein said aryl and heteroaryl are substituted with one to three $R^9$;
$R^4$ is
1) H,
2) $-NR^6S(O)_2R^8$,
3) $(CR_2)_v-S(O)_pR^8$,
4) $C_1$-$C_6$ alkyl,
5) $C_3$-$C_6$ cycloalkyl,
6) $-(CH_2)_{0-1}-CN$,
7) halo,
8) $-C(O)OR^8$,
9) $-NH_2$,
10) $-NO_2$,
11) $-OR$,
12) $-(CR^a_2)_t-S(O)_2R^8$,
13) $-NR^6C(O)R^{10}$,
14) $-NR^6C(O)OR^{10}$,
15) aryl,
16) heterocyclyl, or
17) heteroaryl;
where said alkyl, cycloalkyl, aryl, heterocyclyl or heteroaryl are optionally substituted with one to three OR, $C_1$-$C_6$ alkyl or halo substituents;
$R^5$ is H, aryl, heteroaryl, $C_1$-$C_6$ alkyl, $C_3$-$C_{10}$ cycloalkyl, $C(O)OR$, CN, OR or $S(O)_pR^8$; where said alkyl, cycloalkyl, aryl or heteroaryl are optionally substituted with one to three OR, $CF_3$ or halo substituents;
Each $R^6$ is independently H, $C_1$-$C_6$ alkyl, $C_3$-$C_{10}$ cycloalkyl, heteroaryl or aryl, said alkyl, cycloalkyl, or heteroaryl may be optionally substituted with aryl, heteroaryl or heterocyclyl;
Each $R^8$ is independently $C_1$-$C_6$ alkyl, $C_3$-$C_{10}$ cycloalkyl or aryl, said alkyl, cycloalkyl and aryl are optionally substituted with 1 to 3 $C_3$-$C_{10}$ cycloalkyl or halo substituents;
Each $R^9$ is independently halo, CN, $OCF_3$, $C_1$-$C_6$ alkyl, OR, $NH_2$, aryl or heteroaryl, where said alkyl, aryl or heteroaryl may be optionally substituted with one to three CN, $OCF_3$, OR, $C_1$-$C_6$ alkyl, $NH_2$ or halo substituents;
Each $R^{10}$ is independently H, $C_1$-$C_6$ alkyl, or aryl, said alkyl is optionally substituted with 1-3 halo;
m is 0, 1 or 2;
n is 0, 1, 2 or 3;
p is 0, 1 or 2;
t is 0, 1 or 2;
v is 0, 1, 2 or 3;
x is 0, 1, 2 or 3.
In another embodiment, the invention concerns compounds of Formula I:

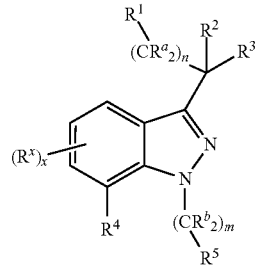

or a pharmaceutically acceptable salt thereof, wherein
Each $R^x$ is independently H, halo, OR, $C_1$-$C_6$ alkyl, $(CR_2)_{0-1}CN$, OR, $C(O)OR^{10}$, $C_3$-$C_{10}$ cycloalkyl, $NR^6C(O)R^{10}$, $NR^6SO_2R^8$, or $NH_2$, said alkyl and cycloalkyl are optionally substituted with 1 to 3 substituents selected from halo, OR and $C_1$-$C_6$ alkyl;
Each R is independently H, $C_1$-$C_6$ alkyl or $C_3$-$C_{10}$ cycloalkyl, said alkyl and cycloalkyl are optionally substituted with 1 to 4 halo substituents;
Each $R^a$ is independently H, $C_1$-$C_6$ alkyl, aryl or $CF_3$, said alkyl and aryl are optionally substituted with 1 to 3 aryl, $CF_3$ or halo substituents;
Each $R^b$ is independently H or $C_1$-$C_6$ alkyl, said alkyl is optionally substituted with 1 to 3 aryl, $CF_3$ or halo substituents;
$R^1$ is
  1) H,
  2) CN,
  3) OR,
  4) $C_1$-$C_6$ alkyl,
  5) $C_3$-$C_6$ cycloalkyl
  6) aryl,
  7) heteroaryl,
  8) heterocyclyl,
  9) $C(O)R^{10}$,
  10) $C(O)NRR^6$, or
  11) $C(O)OR^{10}$;
wherein said alkyl, cycloalkyl, aryl, heteroaryl and heterocyclyl are optionally substituted with one to three $CF_3$, OR, CN, $C_1$-$C_6$ alkyl, or halo substituents;
$R^2$ is
  1) H, or
  2) $C_1$-$C_6$ alkyl, said alkyl is optionally substituted with one to three OR, CN or halo substituents;
$R^3$ is $(CR_2)_t$-aryl or $(CR_2)_t$-heteroaryl, wherein said aryl and heteroaryl are substituted with one to three $R^9$;
$R^4$ is
  1) H,
  2) —$NR^6S(O)_2R^8$,
  3) $(CR_2)_v$—$S(O)_pR^8$,
  4) $C_1$-$C_6$ alkyl,
  5) $C_3$-$C_6$ cycloalkyl,
  6) —$(CH_2)_{0-1}$—CN,
  7) halo,
  8) —$C(O)OR^8$,
  9) —$NH_2$,
  10) —OR,
  11) —$(CR^a_2)_t$—$S(O)_2R^8$,
  12) —$NR^6C(O)R^{10}$,
  13) —$NR^6C(O)OR^{10}$,
  14) aryl,
  15) heterocyclyl, or
  16) heteroaryl;
  where said alkyl, cycloalkyl, aryl, heterocyclyl or heteroaryl are optionally substituted with one to three OR, $C_1$-$C_6$ alkyl or halo substituents;
$R^5$ is H, aryl, heteroaryl, $C_1$-$C_6$ alkyl, $C_3$-$C_{10}$ cycloalkyl, $C(O)OR$, CN, OR or $S(O)_pR^8$; where said alkyl, cycloalkyl, aryl or heteroaryl are optionally substituted with one to three OR, $CF_3$ or halo substituents;
Each $R^6$ is independently H, $C_1$-$C_6$ alkyl, $C_3$-$C_{10}$ cycloalkyl, heteroaryl or aryl, said alkyl, cycloalkyl, or heteroaryl may be optionally substituted with aryl, heteroaryl or heterocyclyl;
Each $R^8$ is independently $C_1$-$C_6$ alkyl, $C_3$-$C_{10}$ cycloalkyl or aryl, said alkyl, cycloalkyl and aryl are optionally substituted with 1 to 3 $C_3$-$C_{10}$ cycloalkyl or halo substituents;

Each $R^9$ is independently halo, CN, $OCF_3$, $C_1$-$C_6$ alkyl, OR, $NH_2$, aryl or heteroaryl, where said alkyl, aryl or heteoaryl may be optionally substituted with one to three CN, $OCF_3$, OR, $C_1$-$C_6$ alkyl, $NH_2$ or halo substituents;
Each $R^{10}$ is independently H, $C_1$-$C_6$ alkyl, or aryl, said alkyl is optionally substituted with 1-3 halo;
m is 0, 1 or 2;
n is 0, 1, 2 or 3;
p is 0, 1 or 2;
t is 0, 1 or 2;
v is 0, 1, 2 or 3;
x is 0, 1, 2 or 3.
In another embodiment of the compounds of Formula I, $R^5$ is H,
m is 0;
and all other variables are as previously defined in Formula I.
In another embodiment of the compounds of Formula I, $R^4$ is $NR^6S(O)_2R^8$ or —$(CR_2)_v$—$S(O)_pR^8$,
$R^5$ is H,
m is 0;
and all other variables are as previously defined in Formula I.
In a further embodiment, a compound which is

| EXAMPLE NO. | Chemical Name |
|---|---|
| 1 | 3-(4-Chloro-2-fluorobenzyl)-1H-indazole and 3-(4-Chloro-2-fluorobenzyl)-7-ethyl-1H-indazole |
| 2 | N-{3-[1-(4-Chloro-2-fluorophenyl)-3-cyanopropyl]-1H-indazol-7-yl}methanesulfonamide (single enantiomer) |
| 3 | 4-(4-Chloro-2-fluorophenyl)-4-(7-pyridin-3-yl-1H-indazol-3-yl)butanenitrile |
| 4 | 4-(4-Chloro-2-fluorophenyl)-4-(7-pyridin-4-yl-1H-indazol-3-yl)butanenitrile |
| 5 | N-{3-[1-(4-Chloro-2-fluorophenyl)-4-hydroxybutyl]-1H-indazol-7-yl}methanesulfonamide |
| 6 | N-{3-[1-(4-Chloro-2-fluorophenyl)-2-cyanoethyl]-1H-indazol-7-yl}methanesulfonamide |
| 7 | N-{3-[1-(4-Chloro-2-fluorophenyl)-3-cyanopropyl]-1H-indazol-7-yl}cyclopropanesulfonamide |
| 8 | N-{3-[1-(4-Chloro-2-fluorophenyl)-3-(3-methyl-1,2,4-oxadiazol-5-yl)propyl]-1H-indazol-7-yl}methanesulfonamide |
| 9 | N-{3-[1-(4-Chloro-2-fluorophenyl)-4-oxopentyl]-1H-indazol-7-yl}methanesulfonamide |
| 10 | N-{3-[1-(4-Chloro-2-fluorophenyl)-4-hydroxy-4-methylpentyl]-1H-indazol-7-yl}methanesulfonamide |
| 11 | N-{3-[1-(4-Chloro-2-fluorophenyl)-4-hydroxy-4-ethylhexyl]-1H-indazol-7-yl}methanesulfonamide |
| 12 | 4-(4-Chloro-2-fluorophenyl)-4-(1H-indazol-3-yl)butanenitrile |
| 13 | 4-(4-Chloro-2-fluorophenyl)-4-(1-methyl-1H-indazol-3-yl)butanenitrile |
| 14 | 4-(4-Chloro-2-fluorophenyl)-4-(1-ethyl-1H-indazol-3-yl)butanenitrile |
| 15 | 4-(4-Chloro-2-fluorophenyl)-4-(1-propyl-1H-indazol-3-yl)butanenitrile |
| 16 | 4-(1-Benzyl-1H-indazol-3-yl)-4-(4-chloro-2-fluorophenyl)butanenitrile |
| 17A | Methyl {3-[1-(4-chloro-2-fluorophenyl)-3-cyanopropyl]-1H-indazol-1-yl}acetate |
| 17B | tert-Butyl {3-[1-(4-chloro-2-fluorophenyl)-3-cyanopropyl]-1H-indazol-1-yl}acetate |
| 17C | Methyl 3-{3-[1-(4-chloro-2-fluorophenyl)-3-cyanopropyl]-1H-indazol-1-yl}propanoate |
| 17D | 4-(4-Chloro-2-fluorophenyl)-4-{1-[(methylsulfanyl)methyl]-1H-indazol-3-yl}butanenitrile |
| 17E | 4-(4-Chloro-2-fluorophenyl)-4-[1-(cyanomethyl)-1H-indazol-3-yl]butanenitrile |
| 17F | 4-(4-Chloro-2-fluorophenyl)-4-[1-(2-methoxyethyl)-1H-indazol-3-yl]butanenitrile |
| 18 | tert-Butyl {3-[1-(4-chlorophenyl)-1-methylethyl]-1H-indazol-1-yl}acetate |

-continued

| EXAMPLE NO. | Chemical Name |
|---|---|
| 19 | Methyl {3-[1-(4-chlorophenyl)-1-ethylpropyl]-1H-indazol-1-yl}acetate |
| 20 | Methyl [3-(4-chlorobenzyl)-1H-indazol-1-yl]acetate |
| 21 | 3-(4-Chlorobenzyl)-1-benzyl-1H-indazole |
| 22 | 2-(4-chlorophenyl)-2-(7-nitro-1H-indazol-3-yl)butanenitrile |
| 23 | N-(3-(1-(4-chlorophenyl)-1-cyanopropyl)-1H-indazol-7-yl)methanesulfonamide |
| 24A | N-(3-(3-(4-chlorophenyl)-2-hydroxypentan-3-yl)-1H-indazol-7-yl)methane sulfonamide(diastereoisomer A) |
| 24B | N-(3-(3-(4-chlorophenyl)-2-hydroxypentan-3-yl)-1H-indazol-7-yl)methane sulfonamide(diastereoisomer B) |
| 25 | N-(3-(2-(4-chlorophenyl)-1-hydroxybutan-2-yl)-1H-indazol-7-yl)methane sulfonamide | or a pharmaceutically acceptable salt thereof.

As used herein except where noted, "alkyl" is intended to include both branched- and straight-chain saturated aliphatic hydrocarbon groups having the specified number of carbon atoms. The term "cycloalkyl" means carbocycles containing no heteroatoms. Examples of cycloalkyl include cyclopropyl, cyclobutyl, cyclopentyl, cyclohexyl, cycloheptyl, decahydronaphthyl and the like. Commonly used abbreviations for alkyl groups are used throughout the specification, e.g. methyl may be represented by conventional abbreviations including "Me" or $CH_3$ or a symbol that is an extended bond without defined terminal group, e.g.

ethyl may be represented by "Et" "Pr" or $CH_2CH_3$, propyl may be represented by $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. If no number is specified, 1-10 carbon atoms are intended for linear or branched alkyl groups. The phrase "$C_{1-6}$ alkyl, wherein the alkyl group may be unsubstituted or substituted with 1-3 fluorine atoms" refers to alkyl groups having 0, 1, 2 or 3 fluorine atoms attached to one or more carbon atoms. The group "$CF_3$", for example, is a methyl group having three fluorine atoms attached the same carbon atom.

"Alkenyl" unless otherwise indicated, means carbon chains which contain at least one carbon-carbon double bond, and which may be linear or branched or combinations thereof. Examples of alkenyl include, but are not limited to, vinyl, allyl, isopropenyl, pentenyl, hexenyl, heptenyl, 1-propenyl, 2-butenyl, 2-methyl-2-butenyl, and the like. The term "cycloalkenyl" means carbocycles containing no heteroatoms having at least one carbon-carbon double bond.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

"Aryl" unless otherwise indicated, means mono- and bicyclic aromatic rings containing 6-12 carbon atoms. Examples of aryl include, but are not limited to, phenyl, naphthyl, indenyl and the like. "Aryl" also includes monocyclic rings fused to an aryl group. Examples include tetrahydronaphthyl, indanyl and the like. The preferred aryl is phenyl.

"Heteroaryl" unless otherwise indicated, means a mono- or bicyclic aromatic ring or ring system having 5 to 10 atoms and containing at least one heteroatom selected from O, S and N. Examples include, but are not limited to, pyrrolyl, isoxazolyl, isothiazolyl, pyrazolyl, pyridyl, pyridinyl, oxazolyl, oxadiazolyl, thiadiazolyl, thiazolyl, imidazolyl, triazolyl, tetrazolyl, furanyl, triazinyl, thienyl, pyrimidyl, pyrimidinyl, pyridazinyl, pyrazinyl, and the like. Heteroaryl also includes aromatic heterocyclic groups fused to heterocycles that are non-aromatic or partially aromatic, and aromatic heterocyclic groups fused to cycloalkyl rings. Additional examples of heteroaryls include, but are not limited to, indazolyl, thienopyrazolyl, imidazopyridazinyl, pyrazolopyrazolyl, pyrazolopyridinyl, imidazopyridinyl and imidazothiazolyl. Heteroaryl also includes such groups in charged form, e.g., pyridinium. In an embodiment, heteroaryl is oxadiazolyl, pyrazolyl, oxazolyl, pyridinyl and imidazolyl "Heterocyclyl", unless otherwise indicated, means a 4-, 5- or 6-membered monocyclic saturated ring containing at least one heteroatom selected from N, S and O, in which the point of attachment may be carbon or nitrogen. Examples of "heterocyclyl" include, but are not limited to, azetidinyl, pyrrolidinyl, piperidinyl, piperazinyl, morpholinyl, oxazolidinyl, imidazolidinyl, 2,3-dihydrofuro(2,3-b)pyridyl, benzoxazinyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

Heterocyclyl moreover includes such moieties in charged form, e.g., piperidinium. In an embodiment, heterocyclyl is pyrrolidinyl, piperidinyl, piperazinyl, morpholinyl and oxazolidinyl.

"Halogen (or halo)" unless otherwise indicated, includes fluorine (fluoro), chlorine (chloro), bromine (bromo) and iodine (iodo). In one embodiment, halo is fluorine or chlorine.

By "oxo" is meant the functional group "=O" which is an oxygen atom connected to the molecule via a double bond, such as, for example, (1) "C=(O)", that is a carbonyl group; (2) "S=(O)", that is, a sulfoxide group; and (3) "N=(O)", that is, an N-oxide group, such as pyridyl-N-oxide.

Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

When any variable (e.g., R, $R^a$, $R^x$, etc.) occurs more than one time in any constituent or in Formula I, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to

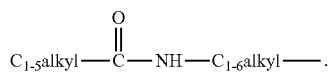

In choosing compounds of the present invention, one of ordinary skill in the art will recognize that the various substituents, i.e. $R^a$, $R^b$, $R^1$, $R^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Where a substituent or variable has multiple definitions, it is understood that the substituent or variable is defined as being selected from the group consisting of the indicated definitions.

Optical Isomers—Diastereoisomers—Geometric Isomers—Tautomers—Atropisomers:

Compounds of structural Formula I may contain one or more asymmetric centers and can thus occur as racemates and racemic mixtures, single enantiomers, diastereoisomeric mixtures and individual diastereoisomers. The present invention is meant to comprise all such isomeric forms of the compounds of structural Formula I.

Compounds of structural Formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer or isomers of a compound of the general structural Formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds of structural Formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural Formula I. For example, different isotopic forms of hydrogen (H) include protium ($^1$H) and deuterium ($^2$H, also denoted as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural Formula I, can be prepared without undue experimentation by conventional techniques well known to those skilled in the art or by processes analogous to those described in the Schemes and Examples herein using appropriate isotopically-enriched reagents and/or intermediates. Thus, the present invention covers isotopically-enriched compounds, including deuterated compounds.

The present invention includes all stereoisomeric forms of the compounds of the Formula I. Centers of asymmetry that are present in the compounds of Formula I can all independently of one another have S configuration or R configuration. The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at the stage of the compounds of the Formula I or at the stage of an intermediate during the synthesis. The present invention also includes all tautomeric forms of the compounds of Formula I.

The present invention includes all atropisomer forms of the compounds of Formula I. Atropisomers are stereoisomers resulting from hindered rotation about single bonds where the steric strain barrier to rotation is high enough to allow for the isolation of the conformers. Atropisomers display axial chirality. Separation of atropisomers is possibly by chiral resolution methods such as selective crystallization.

Salts:

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, benzenesulfonate, benzoate, bicarbonate, bisulfate, bitartrate, borate, bromide, butyrate, camphorate, camphorsulfonate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, methanesulfonate, mucate, napsylate, nitrate, N-methylglucamine ammonium salt, oleate, oxalate, pamoate (embonate), palmitate, pantothenate, phosphate/diphosphate, polygalacturonate, propionate, salicylate, stearate, sulfate, subacetate, succinate, tannate, tartrate, teoclate, thiocyanate, tosylate, triethiodide, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates and the hydrates of the compounds of structural Formula I are included in the present invention as well.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically acceptable salts. The terms "physiologically acceptable salt(s)" and "pharmaceutically acceptable salt(s)" are intended to have the same meaning and are used interchangeably herein.

In an embodiment, the invention concerns compounds of Formula I:

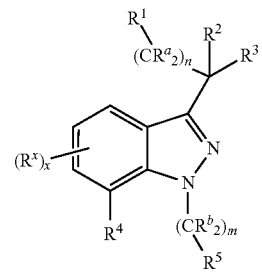

or a pharmaceutically acceptable salt thereof, wherein

Each $R^x$ is independently H, halo, OR, $C_1$-$C_6$ alkyl, $(CR_2)_{0-1}CN$, OR, $C(O)OR^{10}$, $C_3$-$C_{10}$ cycloalkyl, $NR^6C(O)R^{10}$, $NR^6SO_2R^8$, or $NH_2$, said alkyl and cycloalkyl are optionally substituted with 1 to 3 substituents selected from halo, OR and $C_1$-$C_6$ alkyl;

Each R is independently H, $C_1$-$C_6$ alkyl or $C_3$-$C_{10}$ cycloalkyl, said alkyl and cycloalkyl are optionally substituted with 1 to 4 halo substituents;

Each $R^a$ is independently H, $C_1$-$C_6$ alkyl, aryl or $CF_3$, said alkyl and aryl are optionally substituted with 1 to 3 aryl, $CF_3$ or halo substituents;

Each $R^b$ is independently H or $C_1$-$C_6$ alkyl, said alkyl is optionally substituted with 1 to 3 aryl, $CF_3$ or halo substituents;

$R^1$ is
1) H,
2) CN,
3) OR,
4) $C_1$-$C_6$ alkyl,
5) $C_3$-$C_6$ cycloalkyl
6) aryl,
7) heteroaryl,
8) heterocyclyl,
9) $C(O)R^{10}$,
10) $C(O)NRR^6$, or
11) $C(O)OR^{10}$;

wherein said alkyl, cycloalkyl, aryl, heteroaryl and heterocyclyl are optionally substituted with one to three $CF_3$, OR, CN, $C_1$-$C_6$ alkyl, or halo substituents;

$R^2$ is
1) H, or
2) $C_1$-$C_6$ alkyl, said alkyl is optionally substituted with one to three OR, CN or halo substituents;

$R^3$ is $(CR_2)_t$-aryl or $(CR_2)_t$-heteroaryl, wherein said aryl and heteroaryl are substituted with one to three $R^9$;

$R^4$ is
1) H,
2) $NR^6S(O)_2R^8$,
3) —$(CR_2)_v$—$S(O)_pR^8$,
4) $C_1$-$C_6$ alkyl,
5) $C_3$-$C_6$ cycloalkyl,
6) —$(CH_2)_{0-1}$—CN,
7) halo,
8) —$C(O)OR^8$,
9) —$NH_2$,
10) —OR,
11) —$(CR^a_2)_t$—$SO_2R^8$,
12) —$NR^6C(O)R^{10}$,
13) —$NR^6C(O)OR^{10}$,
14) aryl,
15) heterocyclyl, or
16) heteroaryl;
where said alkyl, cycloalkyl, aryl, heterocyclyl or heteroaryl are optionally substituted with one to three OR, $C_1$-$C_6$ alkyl or halo substituents;

$R^5$ is H, aryl, heteroaryl, $C_1$-$C_6$ alkyl, $C_3$-$C_{10}$ cycloalkyl, $C(O)OR$, CN, OR or $S(O)_pR^8$; where said alkyl, cycloalkyl, aryl or heteroaryl are optionally substituted with one to three OR, $CF_3$ or halo substituents;

Each $R^6$ is independently H, $C_1$-$C_6$ alkyl, $C_3$-$C_{10}$ cycloalkyl, heteroaryl or aryl, said alkyl, cycloalkyl, or heteroaryl may be optionally substituted with aryl, heteroaryl or heterocyclyl;

Each $R^8$ is independently $C_1$-$C_6$ alkyl, $C_3$-$C_{10}$ cycloalkyl or aryl, said alkyl, cycloalkyl and aryl are optionally substituted with 1 to 3 $C_3$-$C_{10}$ cycloalkyl or halo substituents;

Each $R^9$ is independently halo, CN, $OCF_3$, $C_1$-$C_6$ alkyl, OR, $NH_2$, aryl or heteroaryl, where said alkyl, aryl or heteroaryl may be optionally substituted with one to three CN, $OCF_3$, OR, $C_1$-$C_6$ alkyl, $NH_2$ or halo substituents;

Each $R^{10}$ is independently H, $C_1$-$C_6$ alkyl, or aryl, said alkyl is optionally substituted with 1-3 halo;

m is 0, 1 or 2;
n is 0, 1, 2 or 3;
p is 0, 1 or 2;
t is 0, 1 or 2;
v is 0, 1, 2 or 3;
x is 0, 1, 2 or 3;

provided at least one of $R^1$, $R^2$, $R^4$, $R^5$, and $R^x$ is not hydrogen.

In an embodiment, $R^1$ is CN, OR, heteroaryl, heterocyclyl or $C_1$-$C_6$ alkyl, said heteroaryl, heterocyclyl, or alkyl is optionally substituted with one to three $CF_3$, OR, CN, $C_1$-$C_6$ alkyl, or halo substituents. In an embodiment, $R^1$ is CN, OR, or $C_1$-$C_6$ alkyl, said heteroaryl, heterocyclyl, or alkyl is optionally substituted with one to three $CF_3$, OR, CN, $C_1$-$C_6$ alkyl, or halo substituents. In an embodiment, $R^1$ is $C_1$-$C_6$ alkyl, said alkyl is optionally substituted with one to three $CF_3$, OR, CN, $C_1$-$C_6$ alkyl, or halo substituents.

In an embodiment, $R^2$ is $C_1$-$C_6$ alkyl, said alkyl is optionally substituted with one to three OR, CN or halo substituents.

In an embodiment, $R^3$ is $(CR_2)_t$-phenyl or $(CR_2)_t$-pyridinyl, wherein said phenyl or pyridinyl is optionally substituted with one to three $R^9$. In an embodiment, $R^3$ is $(CR_2)_t$-phenyl, wherein said phenyl is optionally substituted with one to three $R^9$.

In an embodiment, $R^4$ is
1) $NR^6S(O)_2R^8$,
2) —$(CR_2)_v$—$S(O)_pR^8$,
3) $C_1$-$C_6$ alkyl,
4) $C_3$-$C_6$ cycloalkyl,
5) —$(CH_2)_{0-1}$—CN,
6) halo,
7) —$C(O)OR^8$,
8) —$NH_2$,
9) —OR,
10) —$(CR^a_2)_t$—$SO_2R^8$,
11) —$NR^6C(O)R^{10}$,
12) —$NR^6C(O)OR^{10}$,
13) aryl,
14) heterocyclyl, or
15) heteroaryl;
where said alkyl, cycloalkyl, aryl, heterocyclyl or heteroaryl are optionally substituted with one to three OR, $C_1$-$C_6$ alkyl or halo substituents.

In an embodiment, $R^4$ is —$(CH_2)_{0-1}$—CN, halo, heteroaryl, $NR^6S(O)_2R^8$, or —$(CR_2)_v$—$S(O)_pR^8$, where said heteroaryl is optionally substituted with one to three OR, $C_1$-$C_6$ alkyl or halo substituents. In another embodiment, $R^4$ is $NR^6S(O)_2R^8$, or —$(CR_2)_v$—$S(O)_pR^8$.

The present invention also relates to processes for the preparation of the compounds of Formula I which are described in the following and by which the compounds of the invention are obtainable.

The compounds of the Formula I according to the invention competitively antagonize the aldosterone receptor (MR) and therefore they may be therefore useful agents for the therapy and prophylaxis of disorders related to increased aldosterone levels. The ability for the compounds of Formula I to antagonize MR can be examined, for example, in the activity assay described herein below.

One aspect of the invention that is of interest relates to a compound in accordance with Formula I or a pharmaceutically acceptable salt thereof for use in a method of treatment of the human or animal body by therapy.

Another aspect of the invention that is of interest relates to a compound in accordance with Formula I or a pharmaceutically acceptable salt thereof for use as an anti-hypertensive agent in a human or animal.

Another aspect of the invention that is of interest is a method of treating cardiovascular disease, heart failure, hypertension, atherosclerosis, primary hyperaldosternoism or a related condition in a human patient in need of such treatment comprising administering a therapeutically effective amount of a compound of Formula I or a pharmaceutically acceptable salt thereof.

Another aspect of the invention that is of interest relates to a method of treating metabolic syndrome in a mammal in need of such treatment, comprising administering a therapeutically effective amount of a compound of Formula I or a pharmaceutically acceptable salt thereof.

Another aspect of the invention that is of interest relates to a method of treating a physiological or pathologic disease, selected from including Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, and disorders associated with excess catecholamine levels in a human patient in need of such treatment comprising administering to the patient a therapeutically effective amount of a compound of Formula I or a pharmaceutically acceptable salt thereof.

Another aspect of the invention that is of interest is a method of treating renal failure in a human patient in need of such treatment comprising administering a therapeutically effective amount of a compound of Formula I or a pharmaceutically acceptable salt thereof.

Another aspect of the invention that is of interest is a method of treating hypertension, including, but not limited to, essential hypertension, resistant hypertension, systolic hypertension, pulmonary arterial hypertension, and the like.

Additionally, another aspect of the invention is a method of treating hypertension in an obese animal or human.

Additionally, another aspect of the invention is a method of treating hypertension in a diabetic animal or human.

The compounds of the Formula I and their pharmaceutically acceptable salts can be administered to animals, preferably to mammals, and in particular to humans, as pharmaceuticals by themselves, in mixtures with one another or in the form of pharmaceutical preparations. The term "patient" includes animals, preferably mammals and especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of said disease or medical condition.

A subject of the present invention therefore also are the compounds of the Formula I and their pharmaceutically/physiologically acceptable salts for use as pharmaceuticals, their use for antagonizing mineralocorticoid receptors and in particular their use in the therapy and prophylaxis of the abovementioned syndromes as well as their use for preparing medicaments for these purposes.

A therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention of myocardial infarction.

Furthermore, a subject of the present invention are pharmaceutical preparations (or pharmaceutical compositions) which comprise as active component an effective dose of at least one compound of the Formula I and/or a physiologically/pharmaceutically acceptable salt thereof and a customary pharmaceutically acceptable carrier, i.e., one or more pharmaceutically acceptable carrier substances and/or additives.

Thus, subjects of the invention are, for example, said compound and its pharmaceutically or physiologically acceptable salts for use as a pharmaceutical, pharmaceutical preparations which comprise as an active component a therapeutically effective dose of said compound and/or a physiologically acceptable salt thereof and a customary pharmaceutically acceptable carrier, and the uses of said compound and/or a physiologically acceptable salt thereof in the therapy or prophylaxis of the abovementioned syndromes as well as their use for preparing medicaments for these purposes.

The pharmaceutical compositions according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The amount of active compound of the Formula I and/or its pharmaceutically acceptable salts in the pharmaceutical preparations normally is from 0.2 to 700 mg, preferably from 1 to 500 mg, per dose, but depending on the type of the pharmaceutical preparation it can also be higher. The pharmaceutical preparations usually comprise 0.5 to 90 percent by weight of the compounds of the Formula I and/or their pharmaceutically acceptable salts. The preparation of the pharmaceutical preparations can be carried out in a manner known per se. For this purpose, one or more compounds of the Formula I and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the Formula I and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of the Formula I to be administered and/or of a pharmaceutically acceptable salt thereof depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of the Formula I. In general, a daily dose of approximately 0.01 to 100 mg/kg, preferably 0.01 to 10 mg/kg, in particular 0.3 to 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose.

The compounds of the Formula I bind to the mineralocorticoid receptor and antagonize the biological effects of aldosterone and cortisol. On account of this property, apart from use as pharmaceutically active compounds in human medicine and veterinary medicine, they can also be employed as a scientific tool or as aid for biochemical investigations in which such an effect on the mineralocorticoid receptor is intended, and also for diagnostic purposes, for example in the in vitro diagnosis of cell samples or tissue samples. The compounds of the Formula I and salts thereof can furthermore be employed, as already mentioned above, as intermediates for the preparation of other pharmaceutically active compounds.

The above-mentioned compounds are also of use in combination with other pharmacologically active compounds. Additional active compounds that may be used in combination with the compounds of the instant invention, either co-administered or in a fixed combination, include, but are not limited to, angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan, valsartan, candesartan, olmesartan, telmesartan), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide, chlorthalidone, furosemide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., niacin, HMG Co-A reductase inhibitors), metabolic altering agents including insulin sensitizing agents and related compounds (e.g., muraglitazar, glipizide, metformin, rosiglitazone) or with other drugs beneficial for the prevention or the treatment of the above-mentioned diseases including nitroprusside and diazoxide.

Examples of other active ingredients that may be administered in combination with a compound of Formula I, and either administered separately or in the same pharmaceutical composition, include, but are not limited to:

(a) PPAR gamma agonists and partial agonists, including both glitazones and non-glitazones (e.g. troglitazone, pioglitazone, englitazone, MCC-555, rosiglitazone, balaglitazone, netoglitazone, T-131, LY-300512, LY-818, and compounds disclosed in WO02/08188, WO2004/020408, and WO2004/020409.

(b) biguanides, such as metformin and phenformin;

(c) protein tyrosine phosphatase-1B (PTP-1B) inhibitors;

(d) dipeptidyl peptidase-IV (DPP-4) inhibitors, such as sitagliptin, saxagliptin, vildagliptin, and alogliptin;

(e) insulin or insulin mimetics;

(f) sulfonylureas such as tolbutamide, glimepiride, glipizide, and related materials;

(g) α-glucosidase inhibitors (such as acarbose);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) niacin receptor agonists, nicotinyl alcohol, nicotinic acid, or a salt thereof, (iv) PPARα agonists, such as fenofibric acid derivatives (gemfibrozil, clofibrate, fenofibrate and bezafibrate), (v) cholesterol absorption inhibitors, such as ezetimibe, (vi) acyl CoA:cholesterol acyltransferase (ACAT) inhibitors, such as avasimibe, (vii) CETP inhibitors, such as torcetrapib, anacetrapib, and dalcetrapib, and (viii) phenolic antioxidants, such as probucol;

(i) PPARα/γ dual agonists, such as muraglitazar, tesaglitazar, farglitazar, and JT-501;

(j) PPARδ agonists, such as those disclosed in WO97/28149;

(k) anti-obesity compounds, such as fenfluramine, dexfenfluramine, phentiramine, subitramine, orlistat, neuropeptide Y Y5 inhibitors, MC4R agonists, cannabinoid receptor 1 (CB-1) antagonists/inverse agonists (e.g., rimonabant and taranabant), and β3 adrenergic receptor agonists;

(l) ileal bile acid transporter inhibitors;

(m) agents intended for use in inflammatory conditions, such as aspirin, non-steroidal anti-inflammatory drugs, glucocorticoids, azulfidine, and cyclooxygenase-2 (Cox-2) selective inhibitors;

(n) glucagon receptor antagonists;

(o) GLP-1;

(p) GIP-1;

(q) GLP-1 analogs and derivatives, such as exendins, (e.g., exenatide and liruglatide), and (r) 11β-hydroxysteroid dehydrogenase-1 (HSD-1) inhibitors.

One or more additional active agents may be administered with the compounds described herein. The additional active agent or agents can be lipid modifying compounds or agents having other pharmaceutical activities, or agents that have both lipid-modifying effects and other pharmaceutical activities. Examples of additional active agents which may be employed include but are not limited to HMG-CoA reductase inhibitors, which include statins in their lactonized or dihydroxy open acid forms and pharmaceutically acceptable salts and esters thereof, including but not limited to lovastatin (see U.S. Pat. No. 4,342,767), simvastatin (see U.S. Pat. No. 4,444,784), dihydroxy open-acid simvastatin, particularly the ammonium or calcium salts thereof, pravastatin, particularly the sodium salt thereof (see U.S. Pat. No. 4,346,227), fluvastatin particularly the sodium salt thereof (see U.S. Pat. No. 5,354,772), atorvastatin, particularly the calcium salt thereof (see U.S. Pat. No. 5,273,995), pitavastatin also referred to as NK-104 (see PCT international publication number WO 97/23200) and rosuvastatin, also known as CRESTOR®; see U.S. Pat. No. 5,260,440); HMG-CoA synthase inhibitors; squalene epoxidase inhibitors; squalene synthetase inhibitors (also known as squalene synthase inhibitors), acyl-coenzyme A: cholesterol acyl-transferase (ACAT) inhibitors including selective inhibitors of ACAT-1 or ACAT-2 as well as dual inhibitors of ACAT-1 and -2; microsomal triglyceride transfer protein (MTP) inhibitors; endothelial lipase inhibitors; bile acid sequestrants; LDL receptor inducers; platelet aggregation inhibitors, for example glycoprotein IIb/IIIa fibrinogen receptor antagonists and aspirin; human peroxisome proliferator activated receptor gamma (PPAR-gamma) agonists including the compounds commonly referred to as glitazones for example pioglitazone and rosiglitazone and, including those compounds included within the structural class known as thiazolidine diones as well as those PPAR-gamma agonists outside the thiazolidine dione structural class; PPAR-alpha agonists such as clofibrate, fenofibrate including micronized fenofibrate, and gemfibrozil; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; diuretics (e.g., chlorthalidone, hydrochlorothiazide), sympatholitics, endothelin antagonists; agents that enhance ABCA1 gene expression; cholesteryl ester transfer protein (CETP) inhibiting compounds, including anacetrapib; 5-lipoxygenase activating protein (FLAP) inhibiting compounds, 5-lipoxygenase (5-LO) inhibiting compounds, farnesoid X receptor (FXR) ligands including both antagonists and agonists; Liver X Receptor (LXR)-alpha ligands, LXR-beta ligands, bisphosphonate compounds such as alendronate sodium; cyclooxygenase-2 inhibitors such as rofecoxib and celecoxib; and compounds that attenuate vascular inflammation.

The compounds of Formula I can be synthesized in accordance with the general schemes provided below where $R^1$, $R^2$, and $R^9$ are defined as above (unless otherwise indicated), taking into account the specific examples that are provided. Throughout the synthetic schemes and examples, abbreviations are used with the following meanings unless otherwise indicated:

ABCA1=adenosyltriphosphate-binding cassette-family A1
Ac=acetate, acetyl
aq. is aqueous;
Ar is Aryl;
Bn is benzyl;
Boc is tertbutylcarbamoyl;
br is broad;
Bu is butyl;
$^tBu$ is tert-butyl;
CDI is carbonyl diimidazole;
celite is Celite® diatomaceous earth;
CHO is Chinese hamster ovary
cpm is counts per minute;
OC is degrees Celsius 6 is chemical shift;
$^cPr$ is cyclopropyl;
DCM is dichloromethane;
DIBALH is diisobutylaluminium hydride;
DMF is N,N-dimethylformamide;
DMSO is dimethyl sulfoxide;
EA is ethyl acetate;
EDC is N-(3-dimethylaminopropyl)-N'-ethylcarbodiimide hydrochloride;
EDTA is ethylendiamine tetraacetic acid;
ES-MS is electrospray ion-mass spectroscopy;
Et is ethyl;
$Et_2O$ is diethyl ether;
EtOH is ethanol,
EtOAc is ethyl acetate;
FBS is fetal bovine serum
FXR is farnesoid X receptor;
halo is a halogen (preferably fluorine or chlorine),
HATU is O-(7-azabenzotriazol-1-yl)-N,N,N',N'-tetramethyluronium hexafluorophosphate;
HetAr or HAR is Heteroaryl;
HMG-CoA is 3-hydroxy-3-methyl-glutaryl coenzyme A;
$^1$HNMR is proton nuclear magnetic resonance;
HPLC is high performance liquid chromatography;
Hz is hertz;
i is Iso;
IP is the inflection point for a given dose-response titration curve;
kg is kilogram;
LC/MS is Liquid chromatography/Mass Spectroscopy;
LiHMDS is lithium bis(trimethylsilyl)amide;
$LTB_4$ is leukotriene $B_4$;
LXR is liver X receptor;
M is molar;
Me is methyl;
μg is microgram;
MeCN is acetonitrile;
MeOH is methanol;
MHz is megahertz;
mm is millimeter;
μL is microliter;
mM is milimolar;
μM is micromolar;
mmol is milimoles;
MS is mass spectrum, and a mass spectrum obtained by ES-MS may be denoted herein by "ES";
mw is microwave;
m/z is mass to charge ratio;
n is normal;
NaHMDS is sodium hexamethyldisilazide;
nm is nanometer;
NMM is N-methylmorpholine; nPr is n-propyl;
p is para;
$PdCl_2(PPh_3)_2$ is bis(trisphenylphosphine)palladium(II) dichloride;
$Pd_2(dba)_3$ is tris(dibenzylideneacetone)dipalladium;
$Pd(PPh_3)_4$ is palladium tetrakis(triphenylphosphine);
PE/EA is petroleum ether/ethyl acetate;
Ph is phenyl;
PPARα is peroxisome proliferator activated receptor alpha;
Pr is propyl;

Prep HPLC is preparative HPLC;
Pt/C is platinum carbon;
RP HPLC is Reverse Phase High Performance Liquid Chromatography;
rt is room temperature;
sec is secondary;
'Bu is tert-butyl;
'BuOH is tert-butanol;
TEA is triethyl amine; tert is tertiary;
TFA is trifluoroacetic acid;
THF is tetrahydrofuran;
TLC is thin layer chromatography;
TMSCN is trimethylsilyl cyanide;
U is units
UV is ultraviolet;

Schemes

Reaction schemes 1-12 illustrate the methods employed in the synthesis of the compounds of Formula I. All abbreviations are as defined above unless indicated otherwise. In the Schemes, all substituents are as defined above in Formula I unless indicated otherwise.

Synthetic methods for preparing the compounds of the present invention are illustrated in the following Schemes and Examples. Starting materials are commercially available or may be made according to procedures known in the art or as illustrated herein.

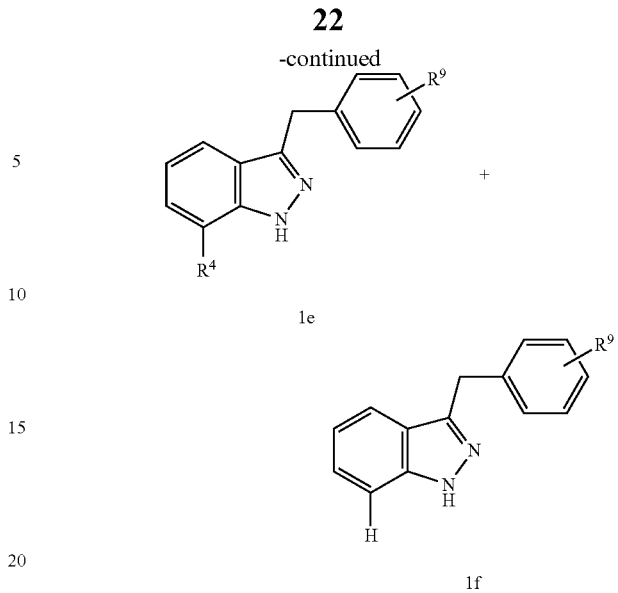

As shown in SCHEME 1, the decarboxylative Claisen reaction of phenyl acetic acid 1b and benzoate 1a provided the ketone intermediate 1c, which then condensed with hydrazine to generate the iodoindazole 1d. The subsequent Suzuki coupling then afforded analogs 1e and the protodehalogenated byproduct 1f.

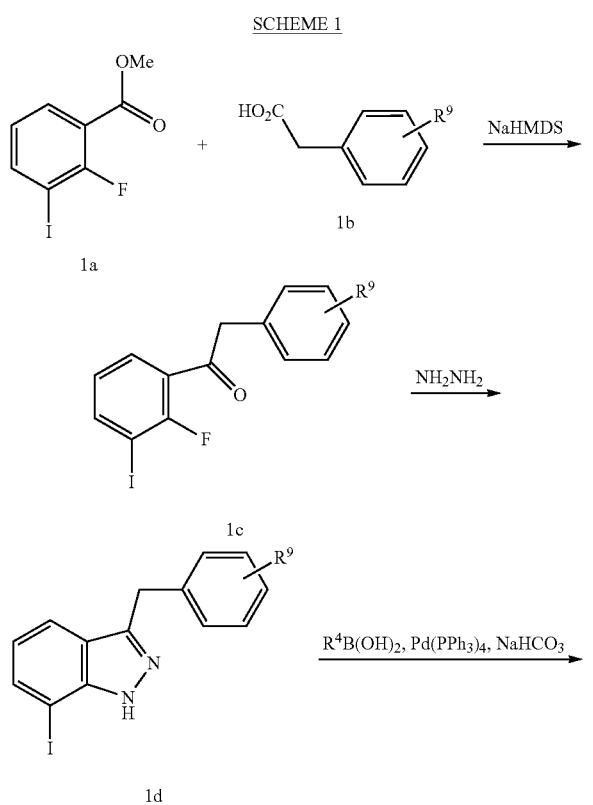

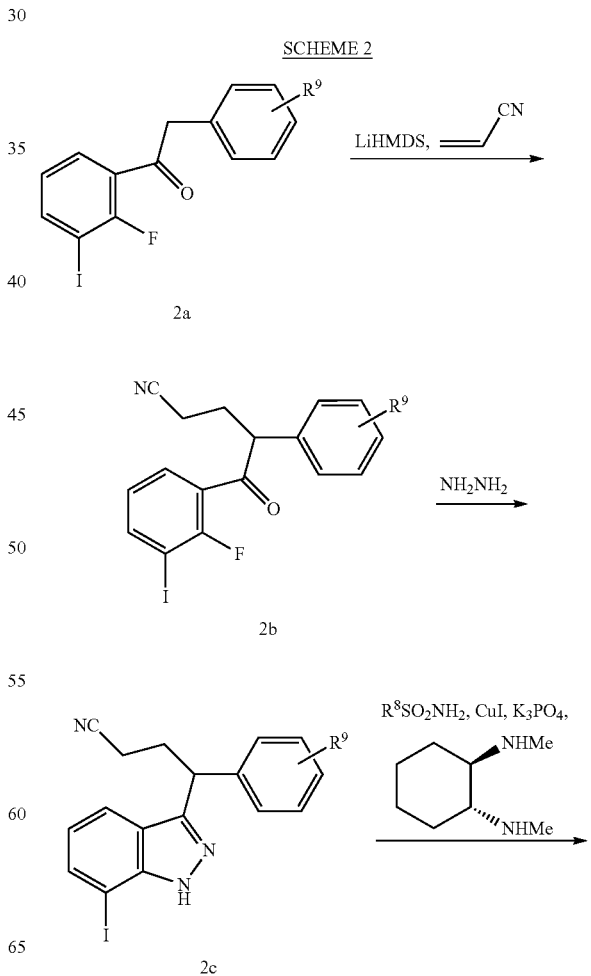

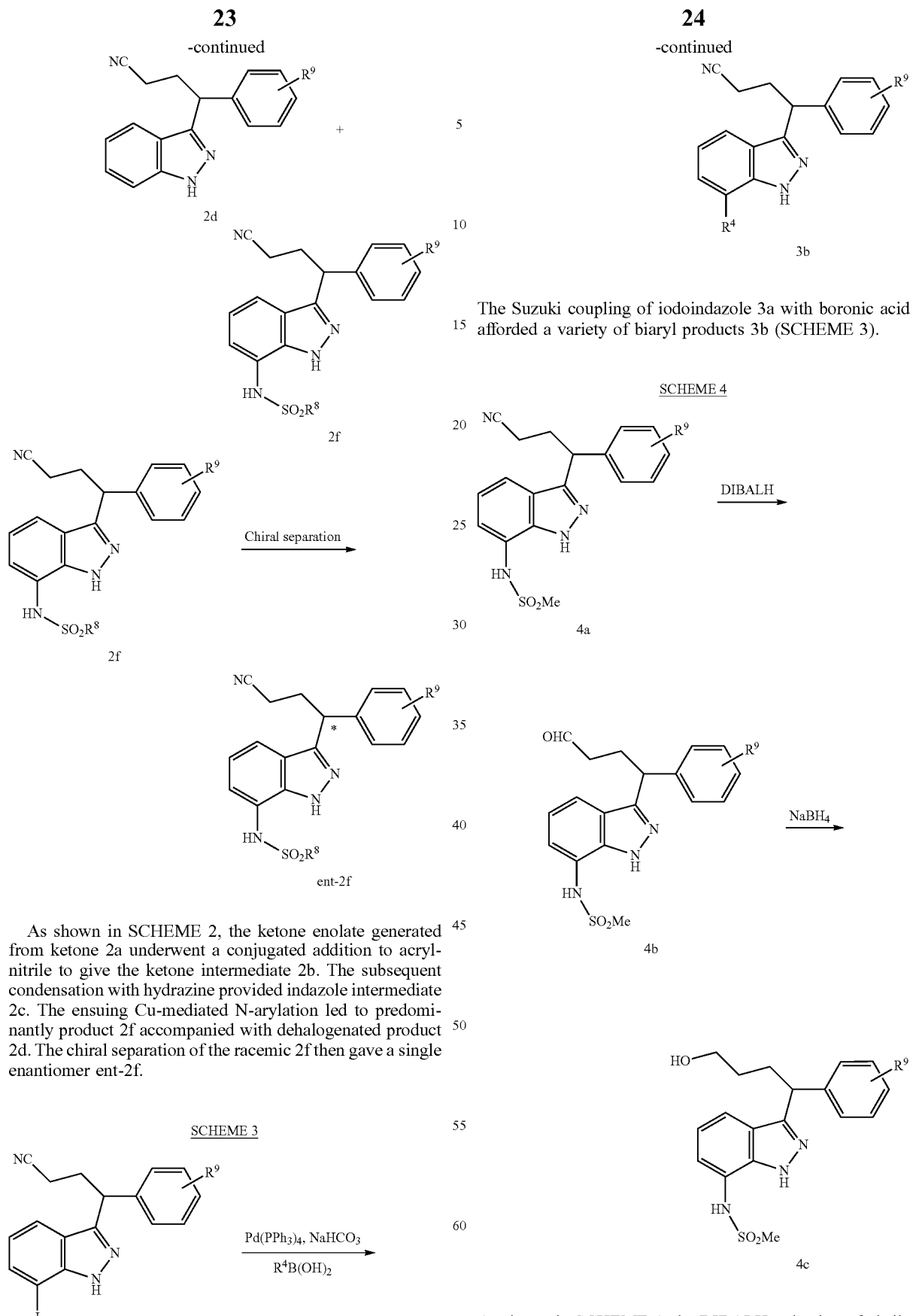

The Suzuki coupling of iodoindazole 3a with boronic acid afforded a variety of biaryl products 3b (SCHEME 3).

As shown in SCHEME 2, the ketone enolate generated from ketone 2a underwent a conjugated addition to acrylnitrile to give the ketone intermediate 2b. The subsequent condensation with hydrazine provided indazole intermediate 2c. The ensuing Cu-mediated N-arylation led to predominantly product 2f accompanied with dehalogenated product 2d. The chiral separation of the racemic 2f then gave a single enantiomer ent-2f.

As shown in SCHEME 4, the DIBALH reduction of nitrile 4a generated aldehyde 4b, which can then be reduced with NaBH$_4$ to give primary alcohol 4c.

SCHEME 5

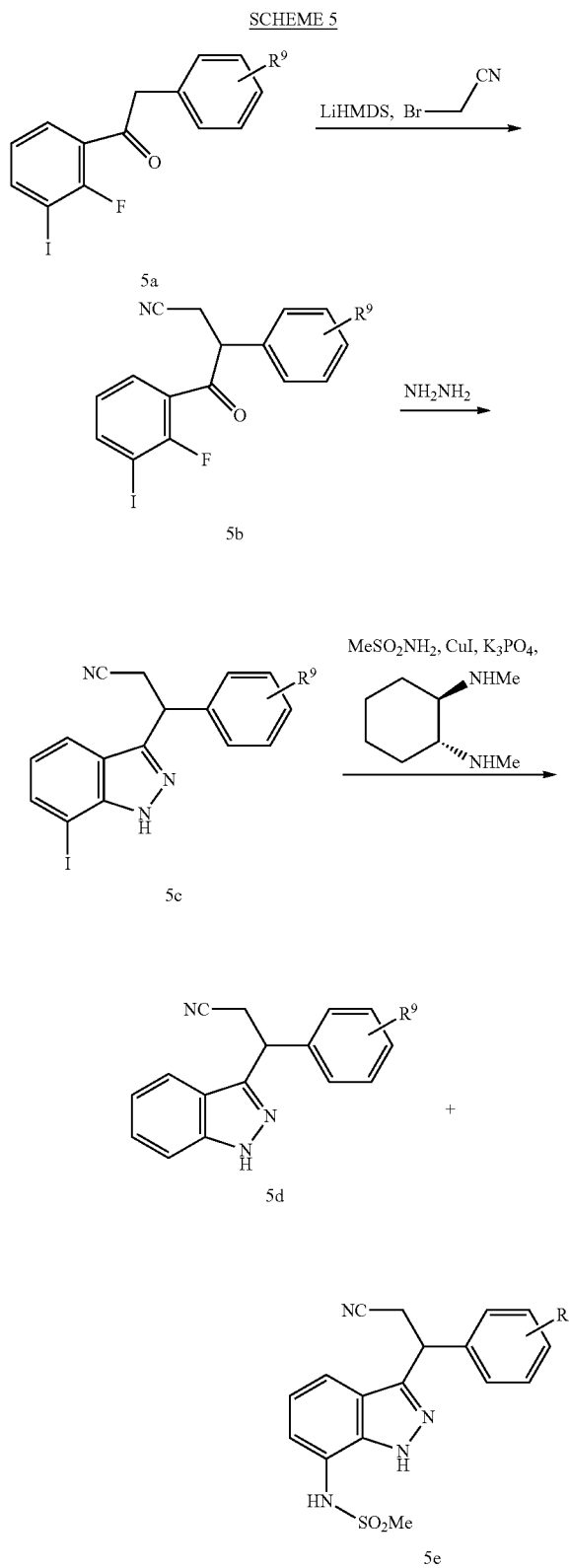

SCHEME 6

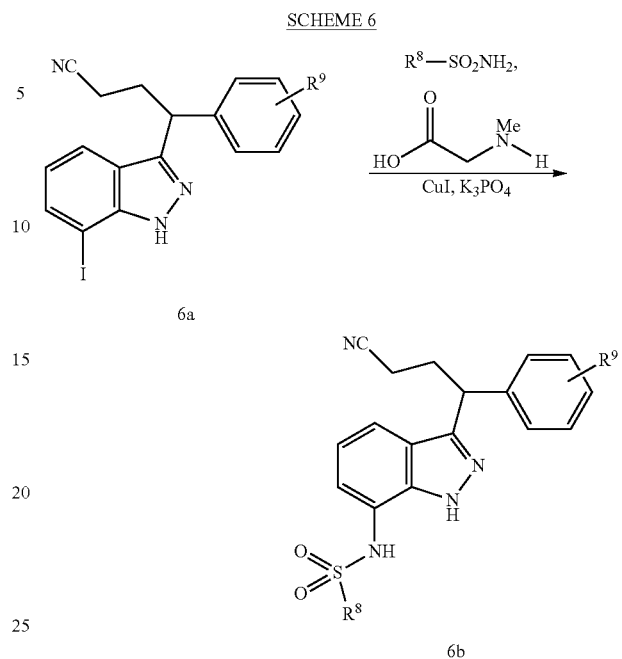

As shown in SCHEME 6, using amino acid as the ligand, the Cu-promoted N-arylation of sulfonamide and iodide 6a provided the desired product 6b.

SCHEME 7

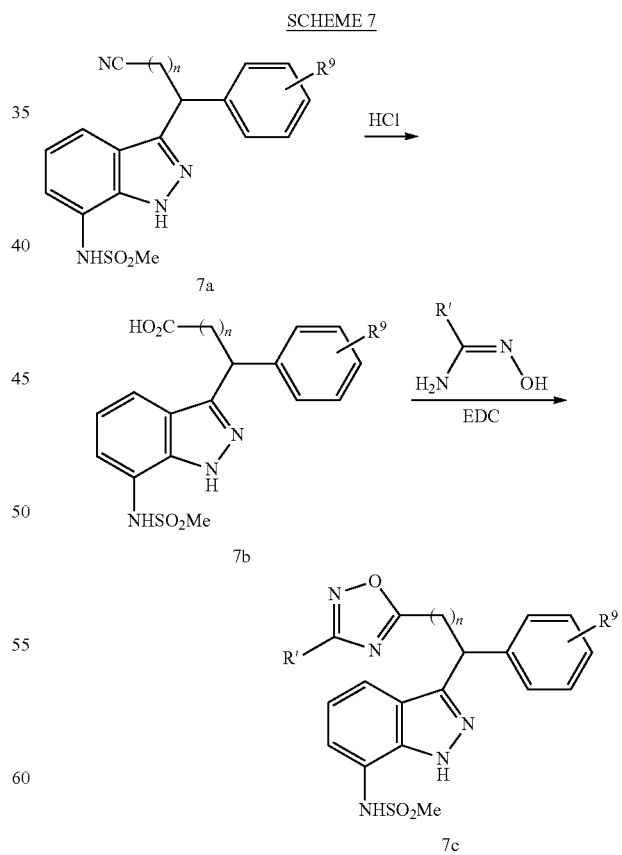

n = 1, 2

R' is CF₃, halo or C₁-C₆ alkyl

As shown in SCHEME 5, the alpha-alkylation of ketone 5a with bromoacetonitrile gave intermediate 5b, which then reacted with hydrazine to give indazole 5c. The subsequent N-arylation then gave analogs 5d and 5e.

As shown in SCHEME 7, the hydrolysis of nitrile 7a gave acid 7b, which then coupled with hydroxyamidine followed by dehydration to yield oxadiazole analogs represented by 7c.

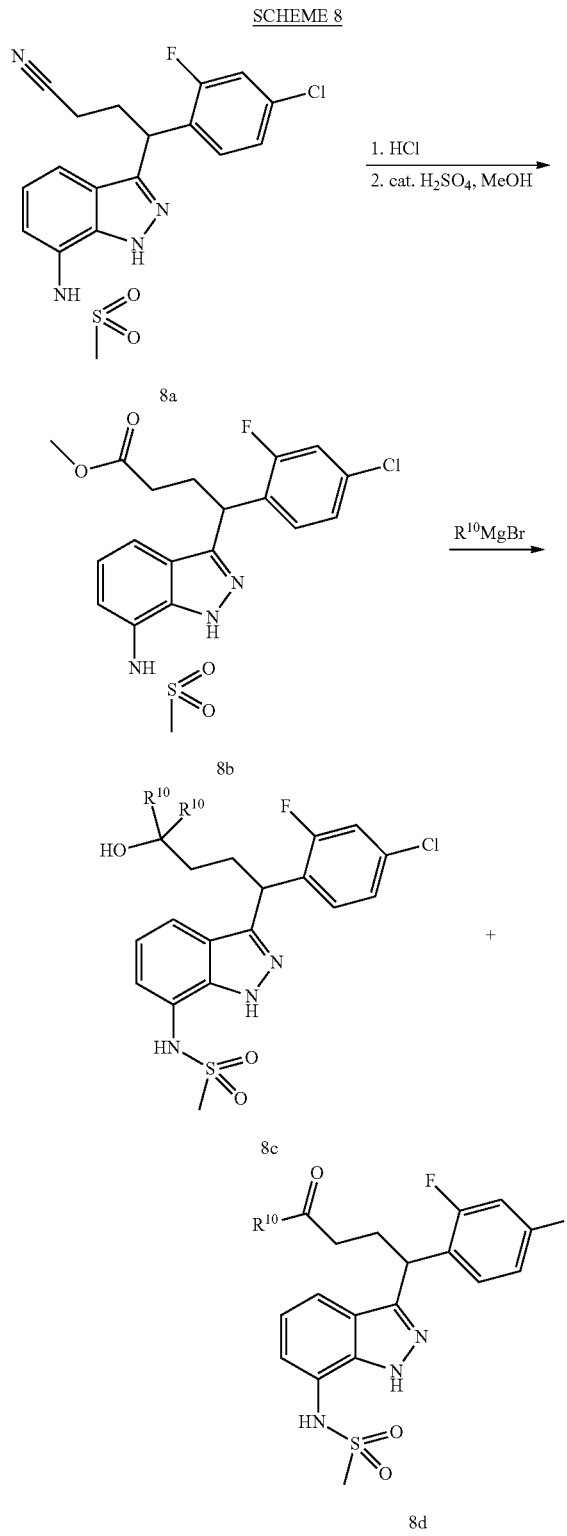

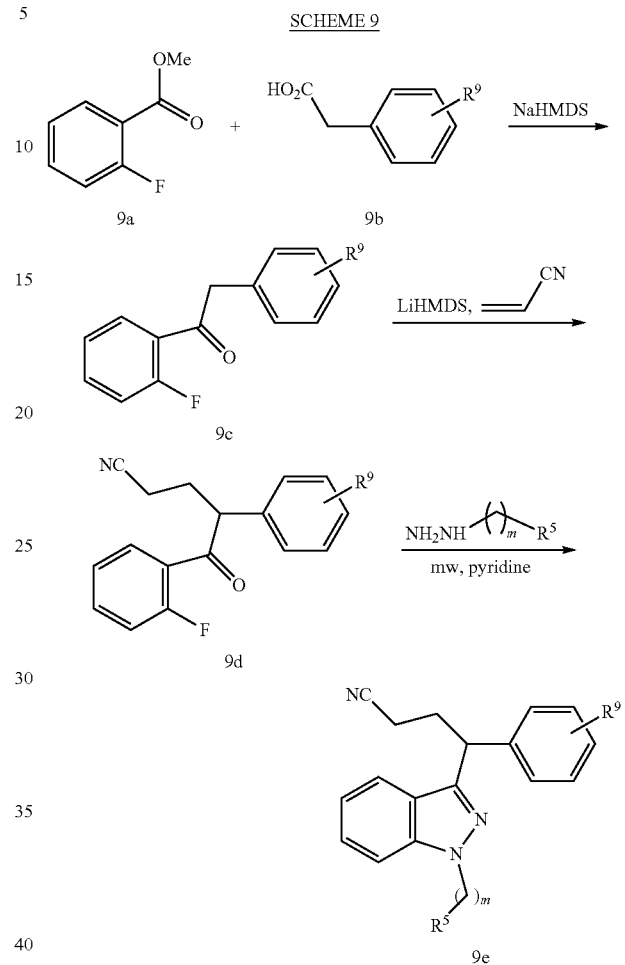

As shown in SCHEME 9, the decarboxylative Claisen reaction of phenyl acetic acid 9b and benzoate 9a provided the ketone intermediate 9c. When treated with base, the enolate generated from ketone 9c underwent a conjugated addition to acrylnitrile to give the ketone intermediate 9d. The subsequent condensation with hydrazine or substituted hydrazines generated indazole 9e.

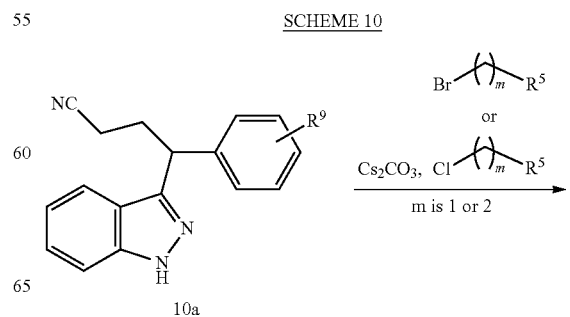

As shown in SCHEME 8, the hydrolysis of nitrile 8a to the corresponding acid followed by acid-catalyzed esterification generated ester 8b. The subsequent Grignard reagent addition gave a mixture of tertiary alcohol 8c and ketone 8d.

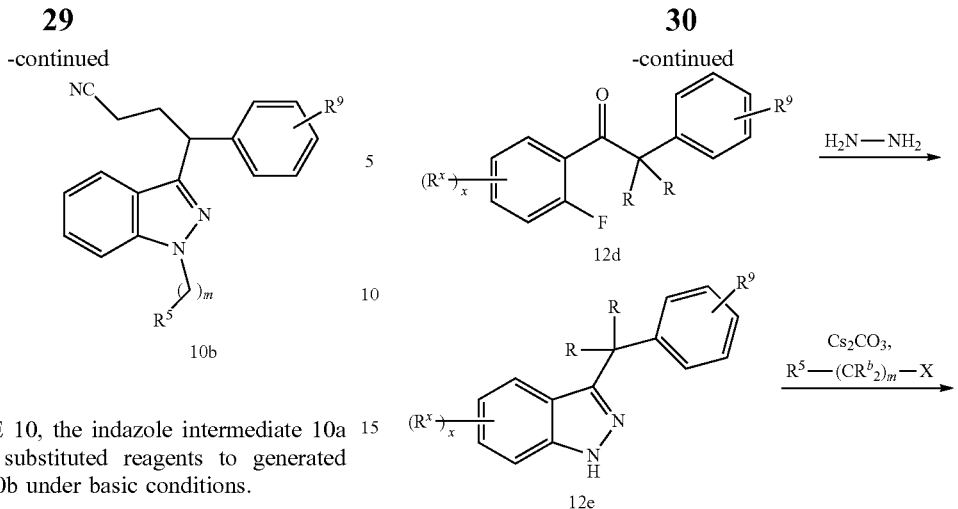

As shown in SCHEME 10, the indazole intermediate 10a reacted with halogen substituted reagents to generated N-alkylated products 10b under basic conditions.

SCHEME 11

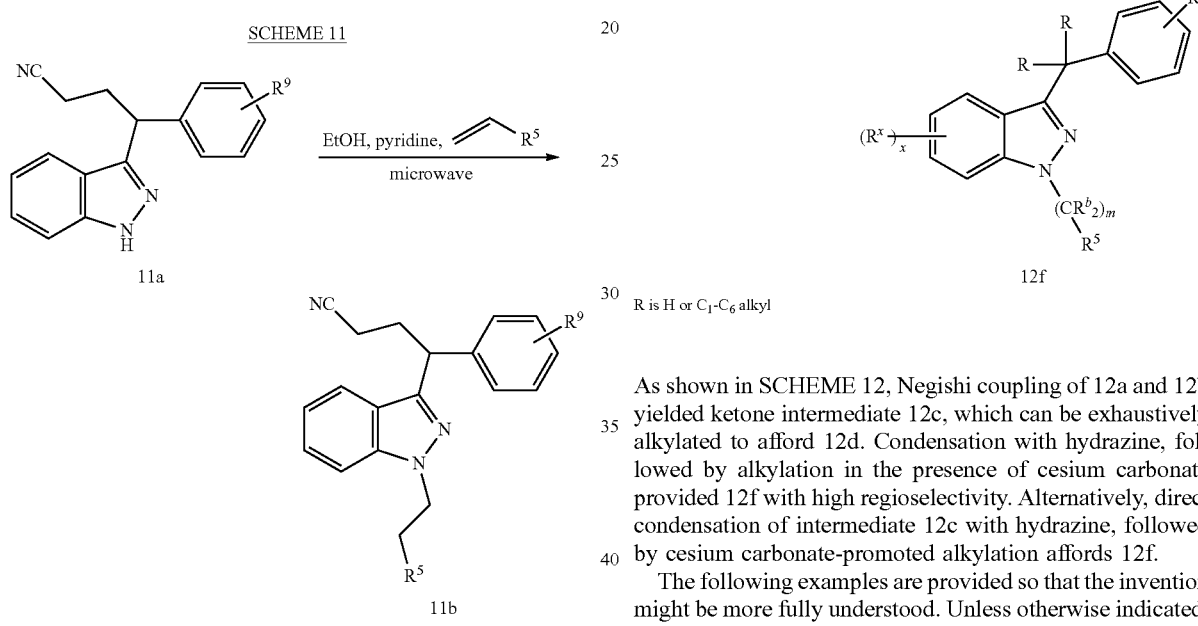

As shown in SCHEME 11, when treated with base under microwave irradiation conditions, indazoles 11a underwent a conjugated addition to unsaturated substrates to give the N-alkylated products 11b.

SCHEME 12

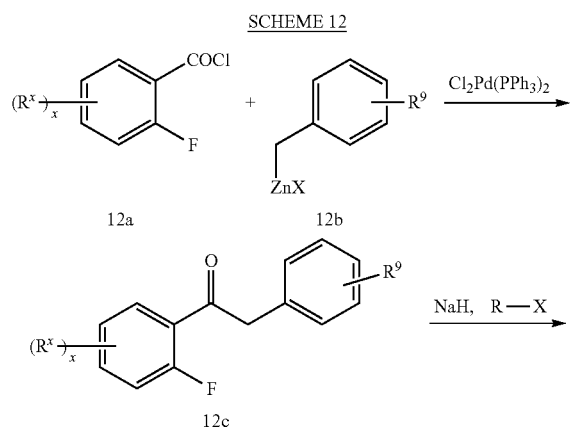

R is H or $C_1$-$C_6$ alkyl

As shown in SCHEME 12, Negishi coupling of 12a and 12b yielded ketone intermediate 12c, which can be exhaustively alkylated to afford 12d. Condensation with hydrazine, followed by alkylation in the presence of cesium carbonate provided 12f with high regioselectivity. Alternatively, direct condensation of intermediate 12c with hydrazine, followed by cesium carbonate-promoted alkylation affords 12f.

The following examples are provided so that the invention might be more fully understood. Unless otherwise indicated, the starting materials are commercially available. They should not be construed as limiting the invention in any way.

REPRESENTATIVE EXAMPLES

The following examples are provided to more fully illustrate the present invention, and shall not be construed as limiting the scope in any manner. Unless stated otherwise:
1) All operations were carried out at room or ambient temperature (rt), that is, at a temperature in the range 18-25° C.;
2) Reactions are generally done using commercially available anhydrous solvents under an inert atmosphere, either nitrogen or argon;
3) Microwave reactions were done using a Biotage Initiator™ or CEM Explorer® system;
4) Evaporation of solvent was carried out using a rotary evaporator under reduced pressure (4.5-30 mmHg) with a bath temperature of up to 50° C.;
5) The course of reactions was followed by thin layer chromatography (TLC) and/or tandem high performance liquid chromatography (HPLC) followed by electron spray mass spectroscopy (MS), herein termed LCMS, and any reaction times are given for illustration only;

6) The structure of all final compounds was assured by at least one of the following techniques: MS or proton nuclear magnetic resonance (1H NMR) spectrometry, and the purity was assured by at least one of the following techniques: TLC or HPLC;
7) $^1$H NMR spectra were recorded on either a Varian Unity or a Varian Inova instrument at 400, 500 or 600 MHz using the indicated solvent; when line-listed, NMR data is in the form of delta values for major diagnostic protons, given in parts per million (ppm) relative to residual solvent peaks (multiplicity and number of hydrogens); conventional abbreviations used for signal shape are: s. singlet; d. doublet (apparent); t. triplet (apparent); m. multiplet; br. broad; etc.;
8) MS data were recorded on a Waters Micromass unit, interfaced with a Hewlett-Packard (Agilent 1100) HPLC instrument, and operating on MassLynx/OpenLynx software; electrospray ionization was used with positive (ES+) or negative ion (ES−) detection; and diode array detection.
9) Purification of compounds by preparative reverse phase HPLC was performed on a Gilson system using a YMC-Pack Pro C18 column (150×20 mm i.d.) eluting at 20 mL/min with a water/acetonitrile (0.1% TFA) gradient (5% acetonitrile to 95% acetonitrile) or on a Shimadzu system using a Sunfire Prep C18 OBD 5 μM column (100×30 mm i.d.) eluting at 50 mL/min with a water/acetonitrile (0.1% TFA) gradient;
10) Purification of compounds by preparative thin layer chromatography (PTLC) was conducted on 20×20 cm glass plates coated with silica gel, commercially available from Analtech; or E. Merck.
11) Flash column chromatography was carried out on a glass silica gel column using Kieselgel 60, 0.063-0.200 mm ($SiO_2$), or on a Biotage $SiO_2$ cartridge system using the Biotage Horizon and Biotage SP-1 systems; or a Teledyne Isco $SiO_2$ cartridge using the CombiFlashRf system;
12) Chemical symbols have their usual meanings, and the following abbreviations have also been used: h (hours), min (minutes), d (days), v (volume), w (weight), b.p. (boiling point), m.p. (melting point), L (liter(s)), mL (milliliters), g (gram(s)), mg (milligrams(s)), mol (moles), mmol (millimoles), eq or equiv (equivalent (s)), IC50 (molar concentration which results in 50% of maximum possible inhibition), EC50 (molar concentration which results in 50% of maximum possible efficacy), μM (micromolar), nM (nanomolar).

In the Tables in the following Examples, compounds having mass spectral data were synthetically prepared.

Example 1

3-(4-chloro-2-fluorobenzyl)-1H-indazole and 3-(4-chloro-2-fluorobenzyl)-7-ethyl-1H-indazole Step A: 2-(4-Chloro-2-fluorophenyl)-1-(2-fluoro-3-iodophenyl)ethanone

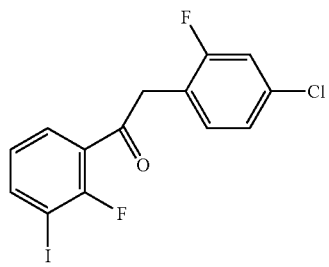 [SMILES: O=C(Cc1ccc(Cl)cc1F)c1cccc(I)c1F]

To methyl 2-fluoro-3-iodobenzoate (6 g) in 60 mL of THF was added NaHMDS (53.6 mL, 1 M in THF) at −78° C. To this mixture was then added (4-chloro-2-fluorophenyl)acetic acid (4 g) as solid in one portion at −78° C. The mixture was stirred at −78° C. for 6 h and then quenched with 3 N HCl at this temperature and stirred at rt for 30 min. The mixture was diluted with ethyl acetate, water. The organic layer was dried and concentrated to 20 mL. 5 mL of hexane was added. The mixture crystallized to give a white solid. 2-(4-Chloro-2-fluorophenyl)-1-(2-fluoro-3-iodophenyl)ethanone was obtained as a white solid collected by filtration.

Step B: 3-(4-Chloro-2-fluorobenzyl)-7-iodo-1H-indazole

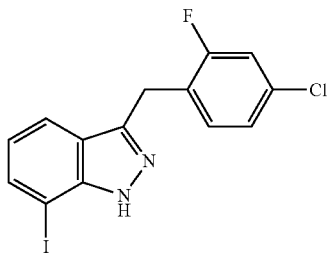 [SMILES: Fc1cc(Cl)ccc1Cc1n[nH]c2c(I)cccc12]

The mixture of 2-(4-Chloro-2-fluorophenyl)-1-(2-fluoro-3-iodophenyl)ethanone (20 mg) and 0.4 mL of hydrazine in 1 mL of pyridine was heated in microwave at 150° C. for 1 h. The mixture was concentrated and purified by Gilson (RP-HPLC, 20-100% Acetonitrile/water/0.1% TFA) to give the desired product 3-(4-chloro-2-fluorobenzyl)-7-iodo-1H-indazole as a white solid. LC/MS 386.9 (M+1).

Step C: 3-(4-chloro-2-fluorobenzyl)-1H-indazole and 3-(4-Chloro-2-fluorobenzyl)-7-ethyl-1H-indazole

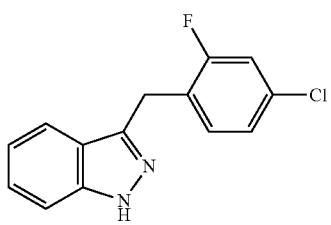 [SMILES: Fc1cc(Cl)ccc1Cc1n[nH]c2ccccc12]

The mixture of 3-(4-chloro-2-fluorobenzyl)-7-iodo-1H-indazole (30 mg) and ethyl boronic acid (29 mg), Pd(PPh$_3$)$_4$ (5 mg), aqueous NaHCO$_3$ solution (0.2 mL, 1 M) and dioxane (2 mL) was heated at 100° C. for 2 h. The resulting mixture was then purified by Gilson (RP-HPLC, 20-100% Acetonitrile/water/0.1% TFA) to give the title compound: 3-(4-chloro-2-fluorobenzyl)-1H-indazole as a byproduct. LC/MS 261.1 (M+1). IP=C rating.

Example 2

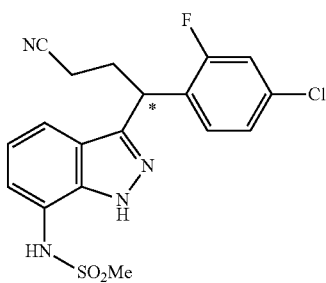 [SMILES: CS(=O)(=O)Nc1cccc2c(C(CCC#N)c3ccc(Cl)cc3F)n[nH]c12]

N-{3-[1-(4-chloro-2-fluorophenyl)-3-cyanopropyl]-1H-indazol-7-yl}methanesulfonamide (Single Enantiomer)

Step A: 4-(4-Chloro-2-fluorophenyl)-5-(2-fluoro-3-iodophenyl)-5-oxopentanenitrile

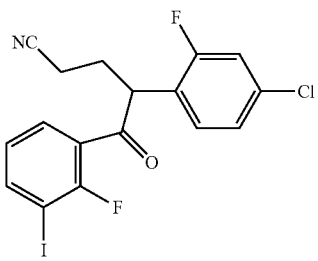 [SMILES: N#CCCC(C(=O)c1cccc(I)c1F)c1ccc(Cl)cc1F]

To 2-(4-chloro-2-fluorophenyl)-1-(2-fluoro-3-iodophenyl)ethanone (4.25 g) in THF (40 mL) at −78° C. was added LiHMDS (1 M, 12 mL). After 30 min at −78° C. to this mixture was added acrylnitrile (2.87 g). The mixture was slowly warmed to rt and stirred overnight. A single more polar spot was identified by TLC (UV). A column eluting with 5-15% ethyl acetate in hexanes gave 4-(4-chloro-2-fluorophenyl)-5-(2-fluoro-3-iodophenyl)-5-oxopentanenitrile as a colorless oil.

Step B: 4-(4-Chloro-2-fluorophenyl)-4-(7-iodo-1H-indazole-3-yl)butanenitrile

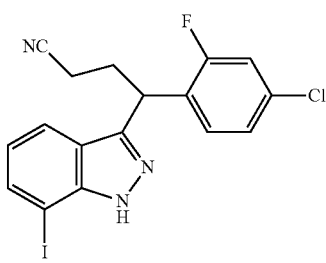 [SMILES: N#CCCC(c1ccc(Cl)cc1F)c1n[nH]c2c(I)cccc12]

The mixture of 4-(4-chloro-2-fluorophenyl)-5-(2-fluoro-3-iodophenyl)-5-oxopentanenitrile (3.42 g) and hydrazine (0.37 g) in 20 mL of pyridine was heated for 30 min at 120° C. After removing the solvent, the residue was crashed in ethyl acetate. The white solid collected was the desired product 4-(4-chloro-2-fluorophenyl)-4-(7-iodo-1H-indazole-3-yl)butanenitrile. LC/MS 439.9 (M+1).

Step C: N-{3-[1-(4-Chloro-2-fluorophenyl)-3-cyanopropyl]-1H-indazol-7-yl}methanesulfonamide (Single Enantiomer)

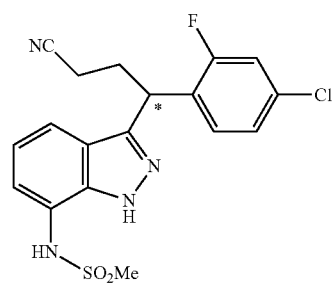 [SMILES: CS(=O)(=O)Nc1cccc2c(C(CCC#N)c3ccc(Cl)cc3F)n[nH]c12]

To 4-(4-chloro-2-fluorophenyl)-4-(7-iodo-1H-indazole-3-yl)butanenitrile (1.70 g) was added methyl sulfonamide (0.44 g), CuI (0.74 g) and K$_3$PO$_4$ (2.46 g). In the glovebox under N$_2$ atmosphere, anhydrous dioxane was added (26 mL) followed by N,N'-dimethylcyclohexyldiamine (1.1 g). The reaction vial was sealed and the reaction was stirred at 110° C. until HPLC indicated full conversion (~16-24 h). To the mixture was added ethyl acetate and water. The organic layer (blue) was filtered and washed with ethyl acetate over a silica gel pad (to remove blue colored salt). The filtrate was concentrated and purified by RP-HPLC (20-100% Acetonitrile/water/0.1% TFA) to give the title product as a racemate white solid. The resulting racemate was then subjected to chiral SFC OJ-H (4.6×250 mm Chiralcel®, 2.1 mL/min, 100 bar, 40% MeOH/CO2, 35° C.). The first elution (early peak, Rt=5.77 min) is the more active single enantiomer MR antagonist. LC/MS 407.0 (M+1). IP=A rating. The second peak (Rt=6.63 min) corresponds to the less active MR antagonist.

Example 3

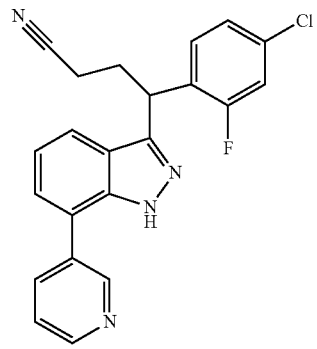 [SMILES: N#CCCC(c1ccc(Cl)cc1F)c1n[nH]c2c(-c3cccnc3)cccc12]

4-(4-chloro-2-fluorophenyl)-4-(7-pyridin-3-yl-1H-indazol-3-yl)butanenitrile

The mixture of racemic 4-(4-chloro-2-fluorophenyl)-4-(7-iodo-1H-indazole-3-yl)butanenitrile (20 mg) and 3-pyridylboronic acid (11 mg) and Pd(PPh₃)₄ (5 mg), NaHCO₃ (0.2 mL, 1 M in water), dioxane (1 mL) was heated at 100° C. for 3 h and the resulting mixture was purified by Gilson (RP-HPLC, 20-100% Acetonitrile/water/0.1% TFA) to give the title compound. LC/MS 391.1 (M+1). IP=C rating.

Example 4

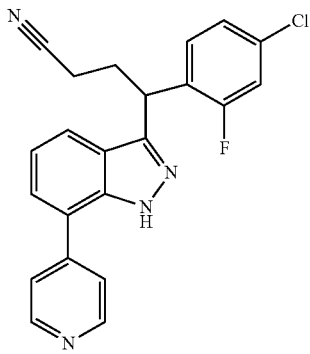 [SMILES: N#CCCC(c1ccc(Cl)cc1F)c1n[nH]c2c(-c3ccncc3)cccc12]

4-(4-chloro-2-fluorophenyl)-4-(7-pyridin-4-yl-1H-indazol-3-yl)butanenitrile

The same procedure as described for the preparation of EXAMPLE 3 was applied to prepare EXAMPLE 4 by replacing 3-pyridylboronic acid with 4-pyridylboronic acid. LC/MS 391.1 (M+1). IP=C rating Example 5

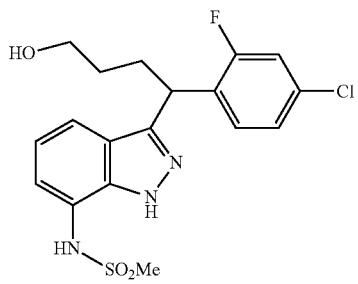

N-{3-[1-(4-chloro-2-fluorophenyl)-4-hydroxybutyl]-1H-indazol-7-yl}methanesulfonamide Step A: N-{3-[1-(4-chloro-2-fluorophenyl)-4-oxobutyl]-1H-indazol-7-yl}methanesulfonamide

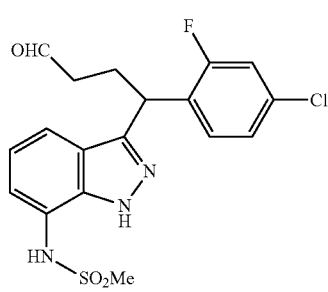 [SMILES: CS(=O)(=O)Nc1cccc2c(C(CCC=O)c3ccc(Cl)cc3F)n[nH]c12]

To racemic N-{3-[1-(4-chloro-2-fluorophenyl)-3-cyanopropyl]-1H-indazol-7-yl}methanesulfonamide (6 mg) in 0.3 mL of DCM at −20° C. was added DIBALH (59 uL, 1 M in DCM). The mixture was slowly warmed to 0° C. and stirred in freezer for 2 days. The resulting mixture was then quenched with 1 N HCl, concentrated and purified by RP-HPLC (20-100% Acetonitrile/water/0.1% TFA) to give N-{3-[1-(4-chloro-2-fluorophenyl)-4-oxobutyl]-1H-indazol-7-yl}methanesulfonamide.

Step B: N-{3-[1-(4-Chloro-2-fluorophenyl)-4-hydroxybutyl]-1H-indazol-7-yl}methanesulfonamide

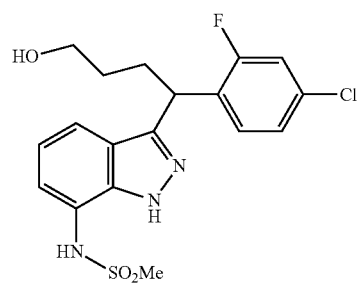 [SMILES: CS(=O)(=O)Nc1cccc2c(C(CCCO)c3ccc(Cl)cc3F)n[nH]c12]

To N-{3-[1-(4-chloro-2-fluorophenyl)-4-oxobutyl]-1H-indazol-7-yl}methanesulfonamide (2.5 mg) in MeOH was added NaBH₄ (2.3 mg) at rt. After 30 min, the mixture was concentrated and purified by RP-HPLC (20-100% Acetonitrile/water/0.1% TFA) to give the title product. LC/MS 411.8 (M+1). IP=B rating.

Example 6

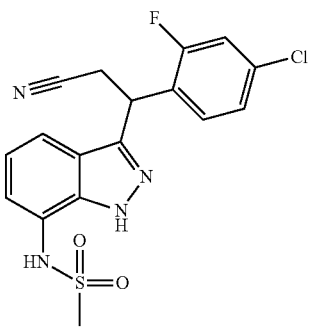 [SMILES: CS(=O)(=O)Nc1cccc2c(C(CC#N)c3ccc(Cl)cc3F)n[nH]c12]

N-{3-[1-(4-chloro-2-fluorophenyl)-2-cyanoethyl]-1H-indazol-7-yl}methanesulfonamide Step A: 3-(4-Chloro-2-fluorophenyl)-4-(2-fluoro-3-iodophenyl)-4-oxobutanenitrile

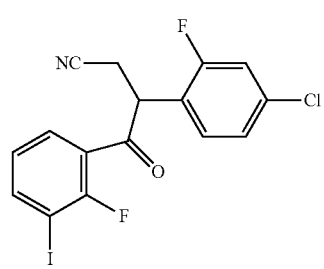 [SMILES: N#CCC(C(=O)c1cccc(I)c1F)c1ccc(Cl)cc1F]

To a solution of 2-(4-chloro-2-fluorophenyl)-1-(2-fluoro-3-iodophenyl)ethanone in THF at −78° C. was added LiH-MDS (1.1 mL, 1 M in THF) dropwise. The mixture was allowed to stir for 30 min before allowing to warm to rt. To the resulting mixture was added bromoacetonitrile (106 µL) dropwise. The reaction mixture was then quenched with water and extracted with EtOAc. The organic layer was washed with water, brine and dried over MgSO₄. After the removal of solvent, the resulting residue was directly used for the next step. LC/MS 431.9 (M+1).

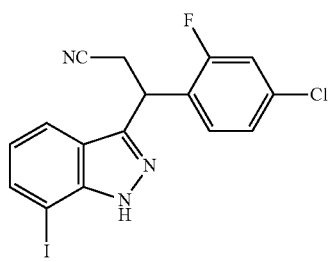 [SMILES: N#CCC(c1ccc(Cl)cc1F)c1n[nH]c2c(I)cccc12]

Step B: 3-(4-Chloro-2-fluorophenyl)-3-(7-iodo-1H-indazol-3-yl)propanenitrile The mixture of 3-(4-chloro-2-fluorophenyl)-4-(2-fluoro-3-iodophenyl)-4-oxobutanenitrile (330 mg) and hydrazine (31 uL) in 2 mL of pyridine was heated at 120° C. for 15 min. The resulting mixture was concentrated, re-dissolved in DMF and purified via Gilson RP-HPLC (20-100% MeCN/water w/0.1% TFA) to give 3-(4-chloro-2-fluorophenyl)-3-(7-iodo-1H-indazol-3-yl)propanenitrile. LC/MS 425.7 (M+1).

Step C: N-{3-[1-(4-chloro-2-fluorophenyl)-2-cyanoethyl]-1H-indazol-7-yl}methanesulfonamide

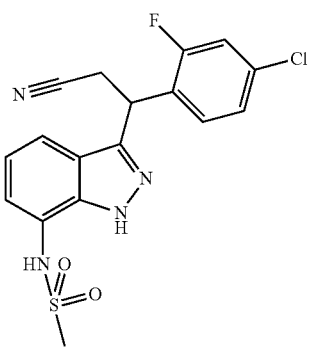 [SMILES: CS(=O)(=O)Nc1cccc2c(C(CC#N)c3ccc(Cl)cc3F)n[nH]c12]

Following the procedure described for the preparation of EXAMPLE 2, 3-(4-chloro-2-fluorophenyl)-3-(7-iodo-1H-indazol-3-yl)propanenitrile was used to prepare the title compound. LC/MS 392.9 (M+1). IP=C rating

Example 7

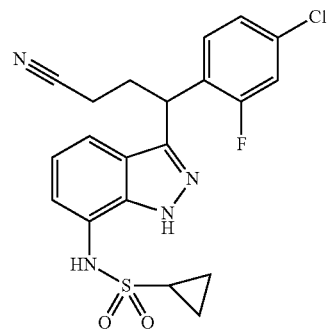 [SMILES: N#CCCC(c1ccc(Cl)cc1F)c1n[nH]c2c(NS(=O)(=O)C3CC3)cccc12]

N-{3-[1-(4-chloro-2-fluorophenyl)-3-cyanopropyl]-1H-indazol-7-yl}cyclopropanesulfonamide To 4-(4-chloro-2-fluorophenyl)-4-(7-iodo-1H-indazole-3-yl)butanenitrile (20 mg), cyclopropylsulfonamide (11 mg), (methylamino)acetic acid (6 mg) and CuI (3 mg), K₃PO₄ (14 mg) was added DMF (1.5 mL). The resulting mixture was heated in a sealed tube under nitrogen at 100° C. for 24 h and then directly purified by RP-HPLC (20-100% MeCN/water w/0.1% TFA) to give the title compound. LC/MS 432.8 (M+1). IP=C rating

Example 8

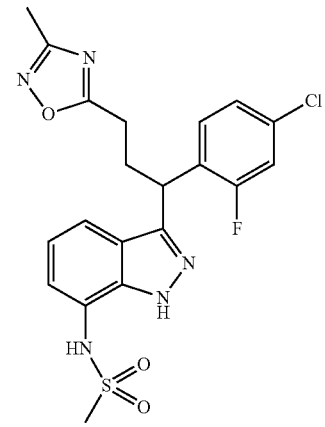 [SMILES: Cc1noc(CCC(c2ccc(Cl)cc2F)c2n[nH]c3c(NS(C)(=O)=O)cccc23)n1]

N-{3-[1-(4-chloro-2-fluorophenyl)-3-(3-methyl-1,2,4-oxadiazol-5-yl)propyl]-1H-indazol-7-yl}methanesulfonamide

Step A: 4-(4-Chloro-2-fluorophenyl)-4-{7-[(methylsulfonyl)amino]-1H-indazol-3-yl}butanoic acid

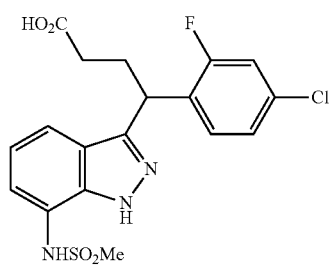

To racemic N-{3-[1-(4-chloro-2-fluorophenyl)-3-cyanopropyl]-1H-indazol-7-yl}methanesulfonamide (30 mg) was added concentrated HCl (1 mL). The mixture was under reflux for 5 h, and then purified via Gilson HPLC (10-100% MeCN/water (w/0.1% TFA v/v)) to give 4-(4-Chloro-2-fluorophenyl)-4-{7-[(methylsulfonyl)amino]-1H-indazol-3-yl)butanoic acid. LC/MS 425.8 (M+1).

Step B: N-{3-[1-(4-Chloro-2-fluorophenyl)-3-(3-methyl-1,2,4-oxadiazol-5-yl)propyl]-1H-indazol-7-yl}methanesulfonamide

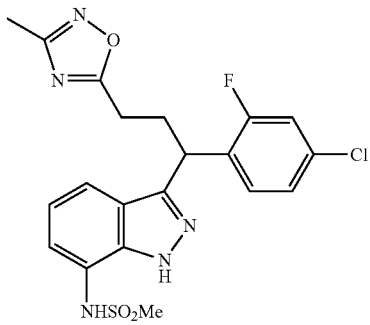

The mixture of 4-(4-chloro-2-fluorophenyl)-4-{7-[(methylsulfonyl)amino]-1H-indazol-3-yl)butanoic acid (10 mg), N'-hydroxyethanimidamide (3 mg), and EDC (7 mg) was stirred in 3 mL of DCM at rt overnight. The solvent was removed and to the residue was added toluene (2 mL). The resulting mixture was heated at 105° C. for 3 h and concentrated. The residue was then purified by RP-HPLC (20-100% MeCN/water w/0.1% TFA) to give the title compound. LC/MS 463.8 (M+1). IP=C rating.

Examples 9 and 10

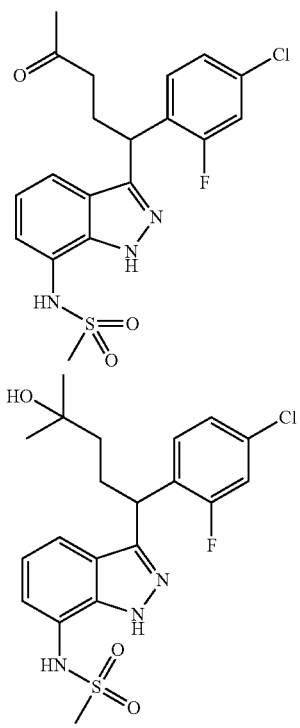

N-{3-[1-(4-chloro-2-fluorophenyl)-4-oxopentyl]-1H-indazol-7-yl}methanesulfonamide and n-{3-[1-(4-chloro-2-fluorophenyl)-4-hydroxy-4-methylpentyl]-1H-indazol-7-yl}methanesulfonamide Step A: Methyl 4-(4-chloro-2-fluorophenyl)-4-(74 (methylsulfonyl)aminol-1-H-indazole-3-yl)butanoate

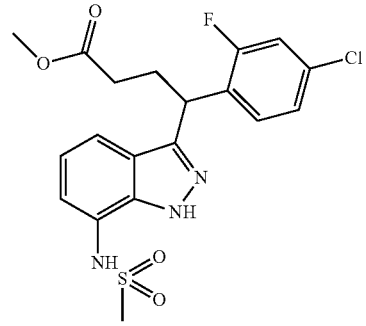

To 4-(4-chloro-2-fluorophenyl)-4-{7-[(methylsulfonyl)amino]-1H-indazol-3-yl)butanoic acid (30 mg) was added 4 uL of concentrated sulfuric acid and MeOH (2 mL). The resulting mixture was under reflux for 2 h to give methyl 4-(4-chloro-2-fluorophenyl)-4-(7-[(methylsulfonyl)amino]-1-H-indazole-3-yl)butanoate. LC/MS 440.0 (M+1).

Step B: N-{3-[1-(4-Chloro-2-fluorophenyl)-4-oxopentyl]-1H-indazol-7-yl}methanesulfonamide and N-{3-[1-(4-chloro-2-fluorophenyl)-4-hydroxy-4-methylpentyl]-1H-indazol-7-yl}methane sulfonamide To methyl 4-(4-chloro-2-fluorophenyl)-4-(7-[(methylsulfonyl)amino]-1-H-indazole-3-yl)butanoate (5 mg) in 2 mL of THF was added methyl magnesium (4 uL, 1 M in THF) at −78° C. The mixture was warmed to 0° C. and then stirred at this temperature fo 2 h before it was quenched with 1 N HCl. The mixture was diluted with ethyl acetate and filtered. The filtrate was purified by RP-HPLC (20-100% MeCN/water w/0.1% TFA) to give the title ketone and alcohol. LC/MS 424.1 (M+1) for the ketone (Example 9, IP=C rating) and LC/MS 422.1 (M−17) for the alcohol (Example 10, IP=C rating).

Example 11

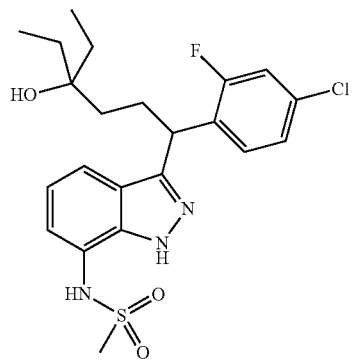 [SMILES: CCC(O)(CC)CCC(c1ccc(Cl)cc1F)c1n[nH]c2c(NS(C)(=O)=O)cccc12]

N-{3-[1-(4-chloro-2-fluorophenyl)-4-hydroxy-4-ethylhexyl]-1H-indazol-7-yl}methanesulfonamide The title compound was prepared using the procedure described in step B of the preparation of EXAMPLE 10, but using ethyl magnesium bromide to react with methyl 4-(4-chloro-2-fluorophenyl)-4-(7-[(methylsulfonyl)amino]-1-H-indazole-3-yl)butanoate. LC/MS 468.2 (M+1). IP=C rating Example 12

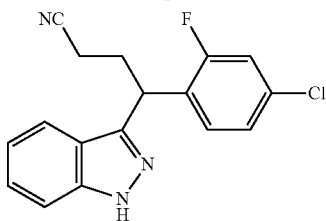 [SMILES: N#CCCC(c1ccc(Cl)cc1F)c1n[nH]c2ccccc12]

4-(4-chloro-2-fluorophenyl)-4-(1H-indazol-3-yl)butanenitrile

Step A: 2-(4-Chloro-2-fluorophenyl)-1-(2-fluorophenyl)ethanone

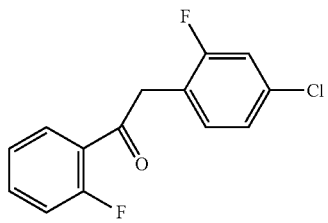 [SMILES: O=C(Cc1ccc(Cl)cc1F)c1ccccc1F]

To methyl 2-fluorobenzoate (300 mg) in 9 mL of THF was added NaHMDS (5.2 mL, 1 M in THF) at −78° C. To this mixture was then added (4-chloro-2-fluorophenyl)acetic acid (367 mg) as solid in one portion at −78° C. The mixture was stirred at −78° C. for 4 h and then quenched with 3 N HCl at this temperature and stirred at rt for overnight. The mixture was diluted with ethyl acetate and water. The organic layer was dried and concentrated to remove solvents. The afforded residue was purified by silica gel flash chromatography (0 to 100% EtOAc/hexane, product out at 25%) to give the desired product 2-(4-Chloro-2-fluorophenyl)-1-(2-fluorophenyl)ethanone as white solid.

Step B: 4-(4-Chloro-2-fluorophenyl)-5-(2-fluorophenyl)-5-oxopentanenitrile

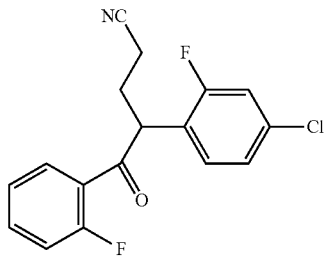 [SMILES: N#CCCC(C(=O)c1ccccc1F)c1ccc(Cl)cc1F]

To 2-(4-chloro-2-fluorophenyl)-1-(2-fluorophenyl)ethanone (300 mg) in THF (10 mL) at −78° C. was added LiHMDS (1 M, 1.1 mL). After 30 min at −78° C. to this mixture was added acrylonitrile (72 mg). The mixture was slowly warmed to rt and stirred overnight. The reaction was quenched with water and extracted with ethyl acetate. The organic layer was dried over Na₂SO₄, filtered and concentrated to remove solvent. The afforded residue was purified by silica gel flash chromatography (0 to 100% EtOAc/hexane, product out at 40%) to give the desired product 4-(4-chloro-2-fluorophenyl)-5-(2-fluorophenyl)-5-oxopentanenitrile as a colorless oil.

Step C: 4-(4-chloro-2-fluorophenyl)-4-(1H-indazol-3-yl)butanenitrile

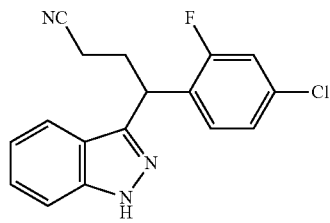 [SMILES: N#CCCC(c1ccc(Cl)cc1F)c1n[nH]c2ccccc12]

The mixture of 4-(4-chloro-2-fluorophenyl)-5-(2-fluorophenyl)-5-oxopentanenitrile (800 mg) and hydrazine (802 mg) in 6 mL of pyridine was heated in microwave at 150° C. for 30 minutes. The mixture was concentrated and purified by silica gel flash chromatography (0 to 100% EtOAc/hexane, product out at 65%) to give the desired product 4-(4-chloro-2-fluorophenyl)-4-(1H-indazol-3-yl)butanenitrile as a colorless oil. LC/MS 314.2 (M+1). IP=C rating Example 13

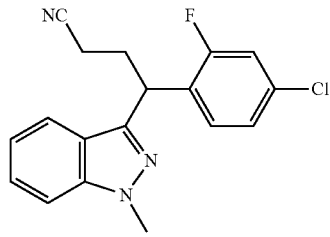 [SMILES: Cn1nc(C(CCC#N)c2ccc(Cl)cc2F)c2ccccc21]

4-(4-chloro-2-fluorophenyl)-4-(1-methyl-1H-indazol-3-yl)butanenitrile

A mixture of 4-(4-chloro-2-fluorophenyl)-5-(2-fluorophenyl)-5-oxopentanenitrile (25 mg) and methylhydrazine (70 mg) in 1 mL of pyridine was heated in microwave at 150° C. for 30 minutes. The mixture was concentrated and purified by reverse phase HPLC to give the desired product 4-(4-chloro-2-fluorophenyl)-4-(1-methyl-1H-indazol-3-yl)butanenitrile. LC/MS 328.3 (M+1). IP=C rating

Example 14

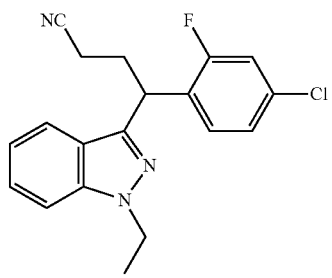 [SMILES: CCn1nc(C(CCC#N)c2ccc(Cl)cc2F)c2ccccc21]

4-(4-chloro-2-fluorophenyl)-4-(1-ethyl-1H-indazol-3-yl)butanenitrile

The mixture of 4-(4-chloro-2-fluorophenyl)-5-(2-fluorophenyl)-5-oxopentanenitrile (25 mg) and ethylhydrazine oxalate (235 mg) in 1 mL of pyridine was heated in microwave at 150° C. for 30 minutes. The mixture was concentrated and purified by reverse phase HPLC to give the desired product 4-(4-chloro-2-fluorophenyl)-4-(1-ethyl-1H-indazol-3-yl)butanenitrile. LC/MS 342.3 (M+1). IP=C rating.

Example 15

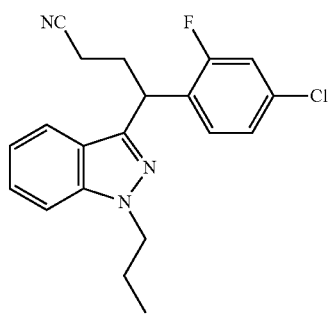 [SMILES: CCCn1nc(C(CCC#N)c2ccc(Cl)cc2F)c2ccccc21]

4-(4-chloro-2-fluorophenyl)-4-(1-propyl-1H-indazol-3-yl)butanenitrile

The mixture of 4-(4-chloro-2-fluorophenyl)-5-(2-fluorophenyl)-5-oxopentanenitrile (25 mg) and propylhydrazine oxalate (257 mg) in 1 mL of pyridine was heated in microwave at 150° C. for 30 minutes. The mixture was concentrated and purified by reverse phase HPLC to give the desired product 4-(4-chloro-2-fluorophenyl)-4-(1-propyl-1H-indazol-3-yl)butanenitrile. LC/MS 356.3 (M+1). IP=C rating

Example 16

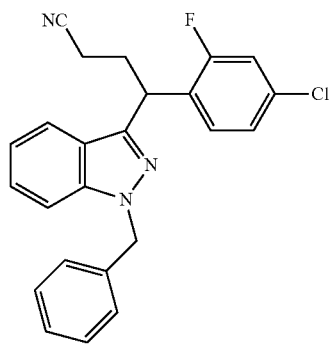 [SMILES: N#CCCC(c1ccc(Cl)cc1F)c1nn(Cc2ccccc2)c2ccccc12]

4-(1-benzyl-1H-indazol-3-yl)-4-(4-chloro-2-fluorophenyl)butanenitrile

The mixture of 4-(4-chloro-2-fluorophenyl)-5-(2-fluorophenyl)-5-oxopentanenitrile (25 mg) and benzylhydrazine dihydrochloride (46 mg) in 1 mL of pyridine was heated in microwave at 150° C. for 30 minutes. The mixture was concentrated and purified by reverse phase HPLC to give the desired product 4-(1-benzyl-1H-indazol-3-yl)-4-(4-chloro-2-fluorophenyl)butanenitrile. LC/MS 404.3 (M+1). IP=C rating

Example 17A

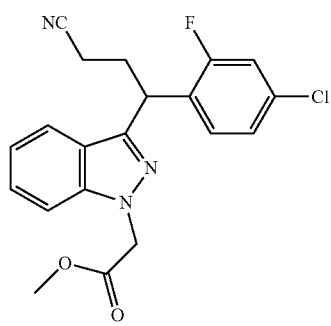 [SMILES: COC(=O)Cn1nc(C(CCC#N)c2ccc(Cl)cc2F)c2ccccc21]

methyl {3-[1-(4-chloro-2-fluorophenyl)-3-cyanopropyl]-1H-indazol-1-yl}acetate

To 4-(4-chloro-2-fluorophenyl)-4-(1H-indazol-3-yl)butanenitrile (30 mg) in DMF (1 mL) was added $Cs_2CO_3$ (93 mg) and methyl bromoacetate (29 mg). The mixture was stirred at room temperature for overnight. The mixture was then filtered and purified with RP-HPLC (10-100% Acetonitrile/water/0.1% TFA) to give the desired product methyl {3-[1-(4-chloro-2-fluorophenyl)-3-cyanopropyl]-1H-indazol-1-yl}acetate. LC/MS 386.1 (M+1). IP=C rating Shown in Table 1 are EXAMPLES 17B-F, which were prepared following the procedures described in EXAMPLE 17A by substituting the corresponding commercially available bromides.

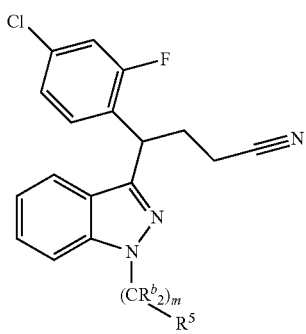

TABLE 1

| Example number | IP (rating) | $(CR^b{}_2)_m R^5$ | Name | LC/MS (M + 1) |
|---|---|---|---|---|
| 17B | C | 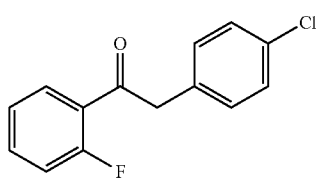 [SMILES: O=C(Cc1ccc(Cl)cc1)c1ccccc1F] | tert-Butyl {3-[1-(4-chloro-2-fluorophenyl)-3-cyanopropyl]-1H-indazol-1-yl}acetate | 372.1 (M − 56) |
| 17C | C | | Methyl 3-{3-[1-(4-chloro-2-fluorophenyl)-3-cyanopropyl]-1H-indazol-1-yl}propanoate | 400.1 |
| 17D | C | | 4-(4-chloro-2-fluorophenyl)-4-{1-[(methylsulfanyl)methyl]-1H-indazol-3-yl}-butanenitrile | 396.0 (M + 23) |
| 17E | C | | 4-(4-chloro-2-fluorophenyl)-4-[1-(cyanomethyl)-1H-indazol-3-yl]-butanenitrile | 353.1 |
| 17F | C | 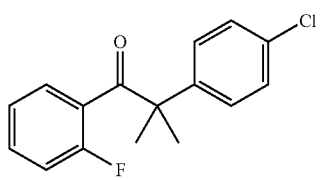 [SMILES: CC(C)(C(=O)c1ccccc1F)c1ccc(Cl)cc1] | 4-(4-chloro-2-fluorophenyl)-4-[1-(2-methoxyethyl)-1H-indazol-3-yl]butanenitrile | 372.1 |

Example 18

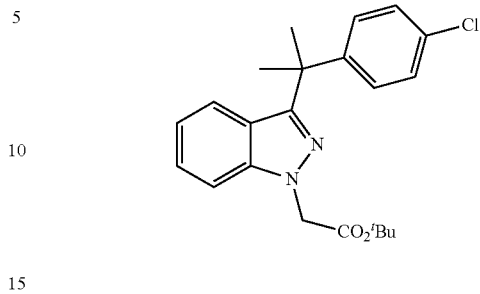

tert-butyl {3-[1-(4-chlorophenyl)-1-methylethyl]-1H-indazol-1-yl}acetate

Step A:
2-(4-chlorophenyl)-1-(2-fluorophenyl)ethanone

To a solution of 2-fluorobenzoyl chloride (1.8 mL) and 4-chlorobenzylzinc chloride (30 mL of a 0.5M THF solution) in THF (35 mL) at 0° C. was added bis(triphenylphosphine)palladium(II) (0.52 g). The resulting mixture was warmed slowly to rt until the reaction was deemed complete.

The mixture was diluted with ethyl acetate and filtered through celite. The filtrate was washed with saturated aqueous ammonium chloride and brine, and purified by column chromatography on silica gel (0-15% ethyl acetate in hexanes as eluent) to afford 2-(4-chlorophenyl)-1-(2-fluorophenyl)ethanone. LC/MS 249.2 (M+1).

Step B: 2-(4-chlorophenyl)-1-(2-fluorophenyl)-2-methylpropan-1-one

To a solution of 2-(4-chlorophenyl)-1-(2-fluorophenyl)ethanone (3.0 g) in DMF (40 mL) at 0° C. was added sodium hydride (0.48 g of a 60% dispersion in mineral spirits). After 15 min, methyl iodide (0.90 mL) was added, and the resulting mixture was allowed to stir at 0° C. for 6 h. The reaction was quenched with water and extracted with ethyl acetate. The organics were washed with water and brine, and purified by column chromatography on silica gel (0-10% ethyl acetate in hexanes as eluent) to afford 2-(4-chlorophenyl)-1-(2-fluorophenyl)-2-methylpropan-1-one. LC/MS 299.2 (M+1).

Step C:
3-[2-(4-chlorophenyl)propan-2-yl]-1H-indazole

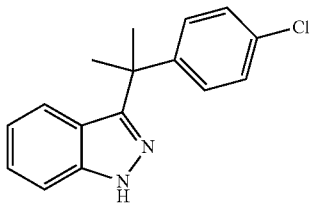 [SMILES: CC(C)(c1ccc(Cl)cc1)c1n[nH]c2ccccc12]

A solution of 3-[2-(4-chlorophenyl)propan-2-yl]-1H-indazole (100 mg) and hydrazine (34 μL) in ethanol (0.7 mL) was heated in a microwave reactor at 160 0 C for 10 min. The reaction was was purified by RP-HPLC (20-80% MeCN/water w/0.1% TFA) to give 3-[2-(4-chlorophenyl)propan-2-yl]-1H-indazole. LC/MS 271.1 (M+1).

Step D: tert-butyl {3-[1-(4-chlorophenyl)-1-methylethyl]-1H-indazol-1-yl}acetate

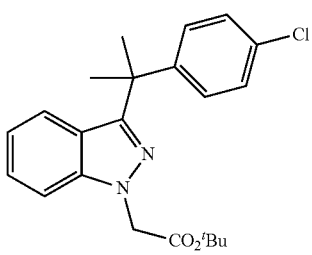 [SMILES: CC(C)(C)OC(=O)Cn1nc(C(C)(C)c2ccc(Cl)cc2)c2ccccc21]

To a solution of 3-[2-(4-chlorophenyl)propan-2-yl]-1H-indazole (30 mg) and cesium carbonate (72 mg) in DMF (0.55 mL) was added tert-butyl bromoacetate (33 μL). After 2 h, the reaction was partitioned between ethyl acetate and water. The organics were purified by column chromatography on silica gel (10-30% ethyl acetate in hexanes as eluent) to afford tert-butyl {3-[1-(4-chlorophenyl)-1-methylethyl]-1H-indazol-1-yl}acetate. LC/MS 329.1 (M-$^t$Bu). IP=C rating Example 19

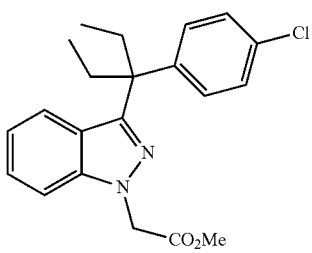 [SMILES: CCC(CC)(c1ccc(Cl)cc1)c1nn(CC(=O)OC)c2ccccc12]

methyl {3-[1-(4-chlorophenyl)-1-ethylpropyl]-1H-indazol-1-yl}acetate

The compound of Example 19 was prepared following procedures similar to those described above for Example 18 by substituting iodoethane for iodomethane in step B, and by subsequently substituting methyl bromoacetate for tert-butyl bromoacetate in step D. LC/MS 371.2 (M+1). IP=B rating Example 20

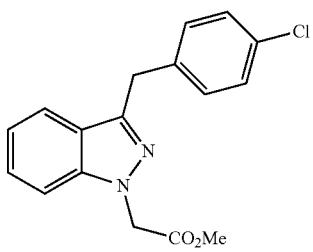 [SMILES: COC(=O)Cn1nc(Cc2ccc(Cl)cc2)c2ccccc21]

Methyl [3-(4-chlorobenzyl)-1H-indazol-1yl]acetate

The compound of Example 20 was prepared following procedures similar to those described above for Example 18 by omitting step B, and subsequently substituting methyl bromoacetate for tert-butyl bromoacetate in step D. LC/MS 315.2 (M+1). IP=C rating Example 21

3-(4-chlorobenzyl)-1-benzyl-1H-indazole

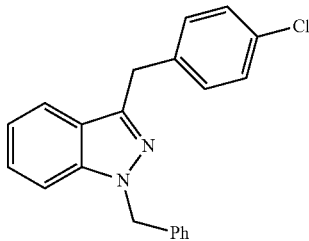 [SMILES: Clc1ccc(Cc2nn(Cc3ccccc3)c3ccccc23)cc1]

The compound of Example 21 was prepared following procedures similar to those described above for Example 18 by omitting step B, and subsequently substituting benzyl bromide for tert-butyl bromoacetate in step D. LC/MS 333.2 (M+1). IP=C rating Example 22

2-(4-chlorophenyl)-2-(7-nitro-1H-indazol-3-yl)butanenitrile (Compound 22)

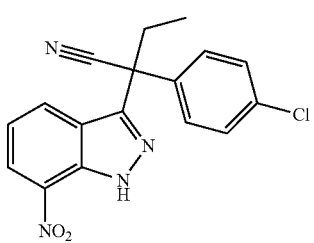 [SMILES: CCC(C#N)(c1ccc(Cl)cc1)c1n[nH]c2c([N+](=O)[O-])cccc12]

Step A: 3-(2-chloro-3-nitrophenyl)-2-(4-chlorophenyl)-3-oxopropanenitrile

A solution of 2-chloro-3-nitrobenzoic acid (201 mg, 1 mmol), CDI (178 mg, 1.1 mmol) in anhydrous DMF (2 mL) was stirred and heated at 50° C. for 1 h. 2-(4-chlorophenyl)

acetonitrile (151 mg, 1 mmol) in anhydrous DMF (2 mL) and NaH (60% dispersion in mineral oil) (126 mg, 3.2 mmol) was added to the mixture at −10° C. The mixture was then stirred at room temperature overnight. The volatile was evaporated. The residue was extracted with ethyl acetate (100 mL). The organic layer was washed with water and brine, dried over sodium sulfate, filtered and evaporated. The residue was purified by silica gel chromatography eluting with PE/EA (5/1 to 1/1, v/v) to afford the title compound as a yellow solid. LC/MS m/z=335.0 [M+H]⁺.

Step B: (E)-3-(2-chloro-3-nitrophenyl)-2-(4-chlorophenyl)-3-ethoxyacrylonitrile

A mixture of the product from Step A above (200 mg, 0.599 mmol), K₂CO₃ (473 mg, 1.198 mmol) and iodoethane (468 mg 1.198 mmol) in DMF (5 mL) was stirred at 80° C. overnight. The volatile was evaporated. The residue was extracted with ethyl acetate (100 mL). The organic layer was washed with water and brine, dried over sodium sulfate, filtered and evaporated. The residue was purified by silica gel chromatography eluting with PE/EA (15/1 to 8/1, v/v) to afford the title compound as a yellow solid. LC/MS m/z=363.0 [M+H]⁺.

Step C: 2-(4-chlorophenyl)-2-(7-nitro-1H-indazol-3-yl)acetonitrile

To a mixture of the product from step B (100 mg, 0.275 mmol), NH₂—NH₂ (0.05 mL), TEA (0.05 mL) in 1,4-dioxane (1 mL) and EtOH (0.15 mL) was heated at 100° C. for 3 h in microwave reactor. The reaction was quenched with saturated ammonium chloride solution, and extracted with ethyl acetate (100 mL). The organic layer was washed with brine, dried over sodium sulfate, filtered and evaporated. The residue was purified by silica gel chromatography eluting with PE/EA (10/1 to 3/1, v/v) to afford the title compound as a yellow solid. LC/MS m/z=313.0 [M+H]⁺.

Step D: 2-(4-chlorophenyl)-2-(7-nitro-1H-indazol-3-yl)butanenitrile

To a mixture of the product from step C (60 mg, 0.192 mmol), iodoethane (36 mg 0.231 mmol) and NaHCO₃ (32.2 mg, 0.384 mmol) in DMF (1 mL) was stirred at room temperature for 1 h. The reaction was quenched with saturated ammonium chloride solution, and extracted with ethyl acetate (50 mL). The organic layer was washed with brine, dried over sodium sulfate, filtered and evaporated. The residue was purified by silica gel chromatography eluting with PE/EA (10/1 to 3/1, v/v) to afford the title compound as a yellow solid. LC/MS m/z=341.0 [M+H]⁺.

TABLE 1

| Compound Number | IP Rating | Structure | IUPAC Name | LCMS m/z [M + H]⁺ |
| --- | --- | --- | --- | --- |
| 22 | C | 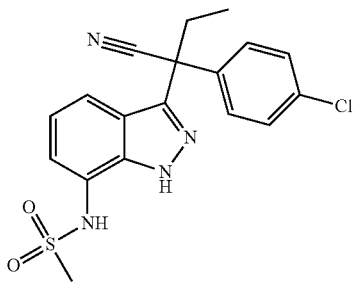 [SMILES: CCC(C#N)(c1ccc(Cl)cc1)c1n[nH]c2c(NS(C)(=O)=O)cccc12] | 2-(4-chlorophenyl)-2-(7-nitro-1H-indazol-3-yl)butanenitrile | 341.0 |

Example 23

N-(3-(1-(4-chlorophenyl)-1-cyanopropyl)-1H-indazol-7-yl)methanesulfonamide (Compound 23)

Step A: 2-(7-amino-1H-indazol-3-yl)-2-(4-chlorophenyl)butanenitrile

To a mixture of 2-(4-chlorophenyl)-2-(7-nitro-1H-indazol-3-yl)butanenitrile (50 mg, 0.147 mmol), as described in Example 22, Step D, in ethyl acetate (2 mL) was added 10% Pt/C (5 mg) and stirred under H₂ atmosphere at room temperature for 2 h. The reaction was filtered and evaporated to afford the title compound as a yellow solid. LC/MS m/z=311.0 [M+H]⁺.

Step B: N-(3-(1-(4-chlorophenyl)-1-cyanopropyl)-1H-indazol-7-yl)methanesulfonamide To a mixture of the product from step A above (45 mg, 0.145 mmol) and NMM (30 mg, 0.29 mmol) in DCM (5 mL) was added methanesulfonyl chloride (25 mg, 0.218 mmol) dropwise. Then the mixture was stirred at room temperature for 4 h. The reaction was quenched with saturated ammonium chloride solution, and extracted with ethyl acetate (50 mL). The organic layer was washed with brine, dried over sodium sulfate, filtered and evaporated. The residue was purified by silica gel chromatography eluting with PE/EA (5/1 to 1/1, v/v) to afford the title compound as a yellow solid. LC/MS m/z=389.0 [M+H]⁺.

TABLE 2

| Compound Number | IP Rating | Structure | IUPAC Name | LCMS m/z [M + H]+ |
|---|---|---|---|---|
| 23 | C | 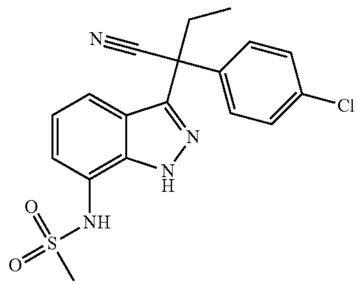 [SMILES: CCC(C#N)(c1ccc(Cl)cc1)c1n[nH]c2c(NS(C)(=O)=O)cccc12] | N-(3-(1-(4-chlorophenyl)-1-cyanopropyl)-1H-indazol-7-yl)methanesulfonamide | 389.0 |

Example 24

N-(3-(3-(4-chlorophenyl)-2-hydroxypentan-3-yl)-1H-indazol-7-yl)methanesulfonamide (Compounds 24A and 24B; diastereoisomers)

Step A: N-(3-(2-(4-chlorophenyl)-1-oxobutan-2-yl)-1H-indazol-7-yl)methanesulfonamide To a mixture of compound N-(3-(1-(4-chlorophenyl)-1-cyanopropyl)-1H-indazol-7-yl)methanesulfonamide (50 mg, 0.129 mmol), as described in Example 23, Step B, in anhydrous DCM (5 mL) was added DIBAL-H (1 M, 0.5 mL, 0.516 mmol) at −78° C. Then the mixture was stirred at room temperature for 4 h. The reaction was quenched with 6N HCl, and extracted with DCM (50 mL). The organic layer was washed with brine, dried over sodium sulfate, filtered and evaporated to afford the title compound as brown oil. LC/MS m/z=392.0 [M+H]+.

Step B: N-(3-(3-(4-chlorophenyl)-2-hydroxypentan-3-yl)-1H-indazol-7-yl)methanesulfonamide To a mixture of the product from step A above (40 mg, 0.102 mmol) in anhydrous THF (5 mL) was added CH₃MgBr (2 M, 0.2 mL, 0.408 mmol) at −78° C. Then the mixture was stirred at room temperature for 4 h. The reaction was quenched with saturated ammonium chloride solution, and extracted with ethyl acetate (50 mL). The organic layer was washed with brine, dried over sodium sulfate, filtered and evaporated. The residue was purified by Prep-HPLC eluting with 0.1% TFA in water and acetonitrile to afford the compound 24A and compound 24B. LC/MS m/z=408.0 [M+H]+.

TABLE 3

| Compound Number | IP Rating | Structure | IUPAC Name | LCMS m/z [M + H]+ |
|---|---|---|---|---|
| 24A | A | 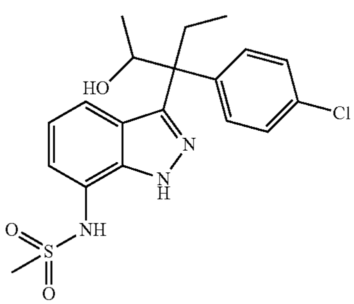 [SMILES: CCC(c1ccc(Cl)cc1)(c1n[nH]c2c(NS(C)(=O)=O)cccc12)C(C)O] | N-(3-(3-(4-chlorophenyl)-2-hydroxypentan-3-yl)-1H-indazol-7-yl)methane sulfonamide(diastereoisomer A) | 408.0 |
| 24B | A | 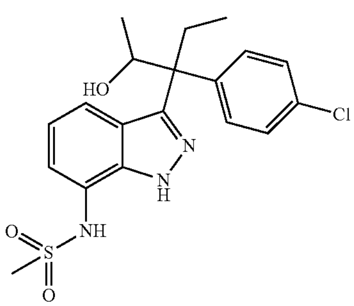 [SMILES: CCC(c1ccc(Cl)cc1)(c1n[nH]c2c(NS(C)(=O)=O)cccc12)C(C)O] | N-(3-(3-(4-chlorophenyl)-2-hydroxypropan-3-yl)-1H-indazol-7-yl)methane sulfonamide(diastereoisomer B) | 408.0 |

Example 25

N-(3-(2-(4-chlorophenyl)-1-hydroxybutan-2-yl)-1H-indazol-7-yl)methanesulfonamide (Compound 25)

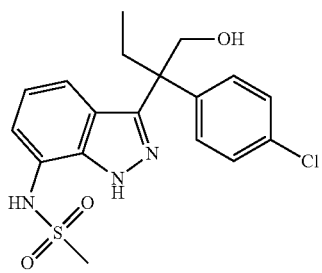 [SMILES: CCC(CO)(c1ccc(Cl)cc1)c1n[nH]c2c(NS(C)(=O)=O)cccc12]

Step A:
2-bromo-6-((4-chlorophenyl)ethynyl)benzenamine

To a solution of 2,6-dibromobenzenamine (27.68 g, 0.11 mol, 1 eq) and 1-chloro-4-ethynylbenzene (15 g, 0.11 mol, 1 eq) was dissolved in $CH_3CN$ (300 mL) was added $PdCl_2$ $(PPh3)_2$ (2 mol %), CuI (1 mol %) and $Et_3N$ (42 mL) as base under $N_2$ atmosphere, the mixture was stirred at 50-60° C. for 20 h, the solvent was evaporated and the residue was dissolved in DCM (400 mL) and filtered, the filtrate was concentrated and the residue was purified on silica gel (PE: EA=2000:20) and concentrated to afford the crude product, which was purified by re-crystallization from 300 mL of petroleum to gave the title compound. TLC $R_f$=0.6 (PE: EA=3:1). LC/MS m/z=306.0 $[M+H]^+$.

Step B:
(7-bromo-1H-indazol-3-yl)(4-chlorophenyl)methanone

To a solution of the product from step A (8.1 g, 26.4 mmol, 1 eq) in dioxane (30 mL) was added $NaNO_2$ (2.43 g, 52.8 mmol, 2 eq), and 60 mL $H_2SO_4$ (20 wt %). The mixture was stirred 0.5 h at −10° C. A solution of diazonium salt was diluted with water (1 L). After 24 h from at 0° C. to room temperature, the precipitate was filtered off, washed with water, and dried to yield pure title compound. LC/MS m/z=335 $[M+H]^+$. $^1$HNMR (400 MHz, $CDCl_3$): δ: 8.27~8.24 (m, 3H), 7.75~7.72 (d, J=12.0 Hz, 1H), 7.65~7.63 (d, J=8.0 Hz, 2H), 7.31~7.27 (t, 1H).

Step C: (7-bromo-1-(4-methoxybenzyl)-1H-indazol-3-yl)(4-chlorophenyl)methanone To a solution of the product from step B (3.4 g, 10 mmol) in DMF (60 mL) was added 4-methoxylbenzyl chloride (3.3 g, 20 mmol, 2 eq) and cesium carbonate (6.5 g, 20 mmol, 2 eq). The mixture was stirred at 50-60° C. for 2 h. Water (120 mL) was added and the mixture was extracted with DCM (40 mL*3). The organic layer was combined and dried over anhydrous $Na_2SO_4$, filtered, concentrated to dryness. The residue was washed by methanol, the filtrate was evaporated under reduce pressure to yield the title compound. TLC $R_f$=0.7 (PE:EA=5:1). LC/MS m/z=455.0 $[M+H]^+$.

Step D: (7-bromo-1-(4-methoxybenzyl)-1H-indazol-3-yl)(4-chlorophenyl)methanol To a suspension of the product from step C (3.2 g, 7.1 mmol) in methanol (80 mL) was added $NaBH_4$ (1.14 g, 31 mmol, 4.36 eq). The mixture was stirred for 3 h at room temperature. The mixture was extracted with ethyl acetate (30 mL*3). The organic layer was combined and dried over anhydrous $Na_2SO_4$, filtered, concentrated to dryness and was purified on silica gel (PE: EA=5:1) to yield the title compound. TLC $R_f$=0.4 (PE: EA=3:1). LC/MS m/z=457.0 $[M+H]^+$. $^1$HNMR (400 MHz, $CDCl_3$): δ: 7.49~7.47 (d, J=8.0 Hz, 1H), 7.38 (m, 3H), 7.30-7.24 (m, 1H), 7.11~7.09 (d, J=8.0 Hz, 1H), 6.89~6.83 (m, 2H), 6.80~6.79 (m, 2H), 6.17 (s, 1H), 5.93 (s, 1H), 3.79 (s, 1H), 3.75 (s, 3H).

Step E: 2-(7-bromo-1-(4-methoxybenzyl)-1H-indazol-3-yl)-2-(4-chlorophenyl) acetonitrile A 100 mL of flask was charged with anhydrous $BiCl_3$ (0.35 g, 1 mmol), dried DCM (10 mL) and TMSCN (3.3 g, 33 mmol, 5 eq) at room temperature. A solution of the product from step D (3 g, 6.6 mmol, 1 eq) was added to the stirred solution and the reaction mixture was stirred overnight. The mixture was washed with saturated aqueous $NaHCO_3$ (50 mL). The organic layer was combined and dried over anhydrous $Na_2SO_4$, filtered, concentrated to dryness. The residue was purified by flash column chromatography on silica gel, eluted with the mixture of PE/AE from 5:1 to 3:1 and yield the title compound (3.2 g, 30% yield). TLC $R_f$=0.8 (PE:EA=10:1). LC/MS m/z=466.0 $[M+H]^+$. $^1$HNMR (400 MHz, $CDCl_3$): δ: 7.47~7.42 (m, 2H), 7.32~7.30 (d, J=8.0 Hz, 2H), 7.26~7.24 (d, J=8.0 Hz, 1H), 7.07~7.05 (d, J=8.0 Hz, 1H), 6.89~6.85 (t, 1H), 6.76-6.73 (d, J=8.0 Hz, 2H), 5.93~5.83 (m, 2H), 5.53 (s, 1H), 3.68 (s, 3H).

Step F: 2-(7-bromo-1-(4-methoxybenzyl)-1H-indazol-3-yl)-2-(4-chlorophenyl) butanenitrile To a solution of the product from step E (3.3 g, 7.1 mmol) in DMF (80 mL) was added ethyl iodide (3.32 g, 21.3 mmol, 3 eq). To the stirred mixture was added 60% sodium hydride (426 mg, 10.65 mmol, 1.5 eq) at ice bath. The mixture was stirred for 30 min. The mixture was quenched by saturated aqueous $NH_4Cl$ and extracted with ethyl acetate (30 mL*3). The organic layer was combined and dried over anhydrous $Na_2SO_4$, filtered, concentrated to dryness. The residue was purified by flash column chromatography on silica gel, eluted with the mixture of PE/AE from 5:1 to 3:1 and yield the title compound. TLC $R_f$=0.8 (PE:EA=10:1). LC/MS m/z=494.0 $[M+H]^+$. $^1$H NMR (400 MHz, $CDCl_3$): δ: 7.43~7.41 (d, J=8.0 Hz, 1H), 7.37~7.35 (d, J=8.0 Hz, 1H), 7.27~7.18 (m, 4H), 7.08~7.06 (d, J=8.0 Hz, 2H), 6.82-6.80 (m, 1H), 6.78~6.75 (m, 2H), 5.92 (s, 2H), 3.70 (s, 3H), 2.80~2.74 (m, 1H), 2.42~2.33 (m, 1H), 1.04-1.01 (m, 3H).

Step G: tert-butyl 3-(1-(4-chlorophenyl)-1-cyanopropyl)-1-(4-methoxybenzyl)-1H-indazol-7-ylcarbamate A dried glass reaction tube equipped with a magnetic stir bar was charged with $Pd_2(dba)_3$ (25 mg, 0.024 mmol, 4 mol %), t-BuXPhos (25 mg, 0.059 mmol, 9.8 mol %), $Cs_2CO_3$ (0.81 g, 2.5 mmol, 1.4 equiv), tert-butyl carbamate (0.3 g, 2.6 mmol, 4.3 equiv), and the product from step F (0.3 g, 0.6 mmol, 1.0 equiv); anhydrous t-BuOH (5.0 mL) was added and the mixture was flushed with nitrogen gas three times. Then the reaction mixture was stirred at 60-80° C. under nitrogen gas overnight until the product from step F were consumed. The solvent was evaporated to dryness, and extracted with ethyl acetate. The combined organic layer was dried with $Na_2SO_4$ and filtered through a pad of Celite.

The filtrate was concentrated in vacuo. The residue was purified by silica gel flash chromatography to produce the title compound. TLC $R_f$=0.6 (PE: EA=5:1). $^1$H NMR (400 MHz, CDCl$_3$): δ: 7.34-7.29 (m, 4H), 7.24~7.22 (d, J=8.0 Hz, 1H), 7.13~7.10 (m, 1H), 7.02~6.93 (m, 3H), 6.82~6.75 (m, 2H), 5.66 (s, 2H), 3.67 (s, 3H), 2.82~2.74 (m, 1H), 2.47~2.38 (m, 1H), 1.43 (s, 8H), 1.05~1.01 (m, 3H).

Step H: 2-(7-amino-1-(4-methoxybenzyl)-1H-indazol-3-yl)-2-(4-chlorophenyl) butanenitrile The mixture of the product from step G (230 mg, 0.43 mmol, 1 eq) and 10 ml of HCl/EA was stirred for 30 min at room temperature. The mixture was extracted with ethyl acetate (10 mL*3). The combined organic layer was washed with saturated aqueous brine, dried over Na$_2$SO$_4$, and concentrated. The product was used for next step without further purification. TLC $R_f$=0.5 (PE:EA=1:1).

Step I: N-(3-(1-(4-chlorophenyl)-1-cyanopropyl)-1-(4-methoxybenzyl)-1H-indazol-7-yl)-N-(methylsulfonyl)methanesulfonamide The product from step H was dissolved in 5 mL of dry CH$_2$Cl$_2$. To the solution was added Et$_3$N (0.26 g, 2.6 mmol, 6 eq) and MsCl (0.25 g, 2.2 mmol, 5 eq) at ice bath. The reaction mixture was stirred for 30 min at room temperature. The mixture was stirred another 1 h at 40~50° C. TLC and LC-MS showed completely converted. The product was separated by prepared TLC. TLC $R_f$=0.7 (PE:EA=5:1). LC/MS m/z=587.0 [M+H]$^+$.

Step J: N-(3-(1-(4-chlorophenyl)-1-cyanopropyl)-1-(4-methoxybenzyl)-1H-indazol-7-yl)methanesulfonamide To a solution of the product from step I (0.2 g, 0.34 mmol) in THF (1 mL) was added an aqueous NaOH (0.8 mL, 10 wt %, 2 mmol, 6 eq). The reaction was stirred for 3 h at 40-50° C. LCMS showed the starting material was consumed. The mixture was extracted with ethyl acetate (10 mL*3). The combined organic layer was washed with saturated aqueous brine, dried over Na$_2$SO$_4$, concentrated to give the title compound. TLC $R_f$=0.3 (PE:EA=3:1). LC/MS m/z=509.0 [M+H]$^+$.

Step K: N-(3-(1-(4-chlorophenyl)-1-cyanopropyl)-1H-indazol-7-yl)methanesulfonamide The mixture of the product from step J (0.16 g, 0.4 mmol, 1 eq) and 5 mL of TFA was stirred for 30 min at 80-100° C. The mixture was extracted with ethyl acetate (10 mL*3). The solvent was evaporated to dryness, basified by an aqueous NaOH (10 wt %) to pH 12, extracted with ethyl acetate. The combined organic layer was dried with Na$_2$SO$_4$ and filtered through a pad of Celite. The filtrate was concentrated in vacuo to give the title compound. TLC $R_f$=0.3 (DCM:MeOH=10:1). LC/MS m/z=389.0 [M+H]$^+$. $^1$HNMR (400 MHz, CDCl$_3$): δ: 7.32 (m, 5H), 7.08 (m, 1H), 6.97 (m, 1H), 2.99 (s, 3H), 2.76 (m, 1H), 2.41 (m, 1H), 1.03 (m, 3H).

Step L: N-(3-(2-(4-chlorophenyl)-1-hydroxybutan-2-yl)-1H-indazol-7-yl)methane sulfonamide To a solution of the product from step K (180 mg, 0.46 mmol, 1 eq) in THF (2 mL) was slowly added DIBALH (9.2 mL, 9.2 mmol, 1M solution in toluene, 20 eq) at −20-10° C. The mixture was stirred for 2 h at room temperature. The reaction was quenched by 1N of aqueous HCl (50 mL), extracted with ethyl acetate (10 mL*3), concentrated. The residue was dissolved in 5 mL of ethanol. To the stirred solution was added NaBH$_4$ (100 mg, 2.64 mmol, 5 eq). The mixture was stirred for another 30 min at room temperature. The final product was purified by Pre-HPLC. LC/MS m/z=394.0 [M+H]$^+$. $^1$HNMR (400 MHz, CDCl$_3$): δ: 7.18-7.26 (m, 5H), 6.79-6.87 (m, 2H), 4.36 (d, 1H, J=11.2), 4.36 (d, 1H, J=11.2), 4.17 (d, 1H, J=11.2), 2.99 (s, 3H), 2.32-2.48 (m, 2H), 0.70 (m, 3H).

TABLE 4

| Compound Number | IP Rating | Structure | IUPAC Name | LCMS m/z [M + H]$^+$ |
| --- | --- | --- | --- | --- |
| 25 | A | (structure) | N-(3-(2-(4-chlorophenyl)-1-hydroxybutan-2-yl)-1H-indazol-7-yl)methane sulfonamide | 394.0 |

Biological Assay

The activity of the compounds of the present invention regarding mineralocorticoid receptor antagonism can be evaluated using the following assay.

Assessment of MR Potency in HMR NH Pro Assay

The human MR NH Pro assay is a commercially available PathHunter™ Protein:Protein interaction assay (DiscoveRx; http://www.discoverx.com/nhrs/prod-nhrs.php) that measures the ability of compounds to antagonize full-length human Mineralocorticoid Receptor (MR) binding to a coactivator peptide. PathHunter™ CHO-K1 cells that overexpress human MR (Cat #93-0456C2, Lot No: 09B0913) were cultured in growth media (F12K w/Glutamine and phenol red (Gibco 11765-047) supplemented with 10% HI FBS (Gibco 16000); 0.25 mg/ml Hygromycin in PBS (Invitrogen 10687-010, 50 mg/ml); 100 I.U./mL and 100 µg/mL Pen/Strep (Gibco 15140-122); 0.6 mg/mL Geneticin (Gibco 10131-027).

Compounds were assessed for MR antagonist activity by incubating the cells with a titrating dose of compound in F12K w/Glutamine and phenol red culture media (Invitrogen 11765-047) supplemented with 1% Charcoal/Dextran Treated FBS (Hyclone #SH30068.01) and aldosterone (0.3 nM to about 1 nM) for 6 hours at 37° C. Cells were then treated with DiscoveRx detection reagent for 1 hour at room temperature and read using an Envision luminescence plate reader. % activity was measured relative to cells treated with aldosterone alone and $IC_{50}$ values were calculated using ADA software.

1. Growth Media:
F12K w/Glutamine and phenol red (Gibco 11765-047)
10% HI FBS (Gibco 16000)
0.25 mg/ml Hygromycin in PBS (Invitrogen 10687-010, 50 mg/ml)
100 I.U./mL and 100 µg/mL Pen/Strep (Gibco 15140-122)
0.6 mg/mL Geneticin (Gibco 10131, 50 mg/ml)
2. Assay media:
F12K w/Glutamine and phenol red (Invitrogen 11765-047)
1% Charcoal/Dextran Treated FBS (Hyclone #SH30068.01)
3. 3× PathHunter Detection Reagents (Cat#93-0001) (need ~6 ml/plate). 19× PathHunter Cell Assay Buffer
5× Emerald II
1× Galacton Star
4. Control Agonist: Aldosterone: Sigma cat# A9477
Stock solution was prepared at 10 µM in DMSO and stored at −20° C. for assay, dilute in assay media to 1.8 or 6 nM (6× of final concentration=about 0.3 nM to about 1.0 nM)
5. Cell line: PathHunter CHO-K1 MR cells Cat #93-0456C2, Lot No: 09B0913, from operation liquid nitrogen stock.
6. Control Antagonist: Spironolactone: Sigma #S-3378 and Eplerenone Sigma #107724-20-9 (10 mM stock concentration also prepared in DMSO and stored at −20° C.).
Methods:
Assay Set up and Calculations:
1. Cells are grown in F12+FBS+Hygromycin+pen/strep+Genetin
2. Cells are collected with 0.05% trypsin and the cell suspension is spun and resuspended in a volume of F12+ 1.5% CD-FBS and counted.
3. The cells concentration was adjusted to $4 \times 10^5$ cells/mL.
4. Cells were (25 µL/well) added to the wells of a 384 well plate.
5. The plate was then incubated at 37° C. over night in a humidified incubator with 5% $CO_2$.
6. Test compounds were titrated starting at 4.4 mM, 10-point titration in 1:3 dilution.
7. Aldosterone was diluted in assay media to 1.8 nM or 6 nM from 10 µM stock (final concentration to be about 0.3 nM to about 1.0 nM)
Protocol for 384 well plate format: 6 hr treatment:
1. 10K exponentially growing cells/well (25 µL) were resuspended in assay media and plated into each well using the Multidrop (Thermo Electron) (use white wall, clear bottom assay plates (Costar #3570) and incubated overnight at 37° C., 5% $CO_2$.
2. 0.25 µL 120× test compound (final DMSO concentration should be <1%) was added to each well n=2, 10 point titrations starting at 36.7 µM final concentration.
3. 5 µL of 6× agonist (final aldosterone concentration should be about 0.3 nM to about 1.0 nM) was added to all wells (using the PlateMate Plus; (ThermoFisher) (except those wells in columns 23 and 24)
4. 5 µL of assay media was added to all wells in column 23 and 24.
5. Cells were then incubated for 6 hrs at 37° C., 5% $CO_2$.
6. 15 µL 3× DiscoveRx detection reagent was then added to to each well.
7. Plates were incubated for 1 hour at room temperature in the dark.
8. Plates were read on Envision (PerkinElmer) luminesence plate reader and analyzed using ADA.
LC/MS method: (LC2M_Low/Med_Positive mode).
LC Conditions: 5-98% $CH_3CN/H_2O$+v 0.1% TFA over 1.25 min; Flow Rate=1.5 mL/min, UV wavelength 254 nm; Column: Waters XTerra® MS C18 3.5 µm 2.1×20 mm IS™

As seen in the Examples above, the tested compounds of the instant invention that had an IP value greater than 0 nM but less than 100 nM were given an "A" rating. Tested compounds of the instant invention that had an IP value equal to, or greater than, 100 nM, but less than 500 nM, were given a "B" rating. Tested compounds of the instant invention that had an IP value equal to, or greater than 500 nM, but less than 6,000 nM, were given a "C" rating.

The invention claimed is:
1. A compound selected from
3-(4-Chloro-2-fluorobenzyl)-1H-indazole and 3-(4-Chloro-2-fluorobenzyl)-7-ethyl-1H-indazole;
N-{3-[1-(4-Chloro-2-fluorophenyl)-3-cyanopropyl]-1H-indazol-7-yl}methanesulfonamide;
4-(4-Chloro-2-fluorophenyl)-4-(7-pyridin-3-yl-1H-indazol-3-yl)butanenitrile;
4-(4-Chloro-2-fluorophenyl)-4-(7-pyridin-4-yl-1H-indazol-3-yl)butanenitrile;
N-{3-[1-(4-Chloro-2-fluorophenyl)-4-hydroxybutyl]-1H-indazol-7-yl}methanesulfonamide;
N-{3-[1-(4-Chloro-2-fluorophenyl)-2-cyanoethyl]-1H-indazol-7-yl}methanesulfonamide;
N-{3-[1-(4-Chloro-2-fluorophenyl)-3-cyanopropyl]-1H-indazol-7-yl}cyclopropanesulfonamide;
N-{3-[1-(4-Chloro-2-fluorophenyl)-3-(3-methyl-1,2,4-oxadiazol-5-yl)propyl]-1H-indazol-7-yl}methanesulfonamide;
N-{3-[1-(4-Chloro-2-fluorophenyl)-4-oxopentyl]-1H-indazol-7-yl}methanesulfonamide;
N-{3-[1-(4-Chloro-2-fluorophenyl)-4-hydroxy-4-methylpentyl]-1H-indazol-7-yl}methanesulfonamide;
N-{3-[1-(4-Chloro-2-fluorophenyl)-4-hydroxy-4-ethylhexyl]-1H-indazol-7-yl}methanesulfonamide;
4-(4-Chloro-2-fluorophenyl)-4-(1H-indazol-3-yl)butanenitrile;
4-(4-Chloro-2-fluorophenyl)-4-(1-methyl-1H-indazol-3-yl)butanenitrile;
4-(4-Chloro-2-fluorophenyl)-4-(1-ethyl-1H-indazol-3-yl)butanenitrile;
4-(4-Chloro-2-fluorophenyl)-4-(1-propyl-1H-indazol-3-yl)butanenitrile;
4-(1-Benzyl-1H-indazol-3-yl)-4-(4-chloro-2-fluorophenyl)butanenitrile;
Methyl {3-[1-(4-chloro-2-fluorophenyl)-3-cyanopropyl]-1H-indazol-1-yl}acetate;
tert-Butyl {3-[1-(4-chloro-2-fluorophenyl)-3-cyanopropyl]-1H-indazol-1-yl}acetate;
Methyl 3-{3-[1-(4-chloro-2-fluorophenyl)-3-cyanopropyl]-1H-indazol-1-yl}propanoate;

4-(4-Chloro-2-fluorophenyl)-4-{1-[(methylsulfanyl)methyl]-1H-indazol-3-yl}butanenitrile;

4-(4-Chloro-2-fluorophenyl)-4-[1-(cyanomethyl)-1H-indazol-3-yl]butanenitrile;

4-(4-Chloro-2-fluorophenyl)-4-[1-(2-methoxyethyl)-1H-indazol-3-yl]butanenitrile;

tert-Butyl {3-[1-(4-chlorophenyl)-1-methylethyl]-1H-indazol-1-yl}acetate;

Methyl {3-[1-(4-chlorophenyl)-1-ethylpropyl]-1H-indazol-1-yl}acetate;

Methyl [3-(4-chlorobenzyl)-1H-indazol-1-yl]acetate; and 3-(4-Chlorobenzyl)-1-benzyl-1H-indazole;

or a pharmaceutically acceptable salt thereof.

2. A pharmaceutical composition comprised of the compound of claim 1 and a pharmaceutically acceptable carrier.

3. The pharmaceutical composition of claim 2 comprising one or more pharmaceutically active agents in addition to the compound of claim 1.

4. A method for antagonizing aldosterone receptor (MR) and increasing aldosterone levels comprising administering an amount efficacious therefore of the compound of claim 1.

* * * * *